US009949723B2

(12) United States Patent
Oh et al.

(10) Patent No.: US 9,949,723 B2
(45) Date of Patent: Apr. 24, 2018

(54) IMAGE PROCESSING APPARATUS, MEDICAL IMAGE APPARATUS AND IMAGE FUSION METHOD FOR THE MEDICAL IMAGE

(71) Applicant: SAMSUNG ELECTRONICS CO., LTD., Suwon-si (KR)

(72) Inventors: Young Taek Oh, Seoul (KR); Jung Woo Chang, Seoul (KR); Ja Yeon Jeong, Yongin-si (KR); Won-Chul Bang, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 98 days.

(21) Appl. No.: 14/933,164

(22) Filed: Nov. 5, 2015

(65) Prior Publication Data
US 2016/0174945 A1 Jun. 23, 2016

(30) Foreign Application Priority Data
Dec. 23, 2014 (KR) .................. 10-2014-0187456

(51) Int. Cl.
*G06K 9/00* (2006.01)
*A61B 8/08* (2006.01)
*A61B 6/03* (2006.01)
*A61B 6/00* (2006.01)
*A61B 8/00* (2006.01)
*G06T 11/00* (2006.01)
(Continued)

(52) U.S. Cl.
CPC ............ *A61B 8/5261* (2013.01); *A61B 6/032* (2013.01); *A61B 6/5247* (2013.01); *A61B 8/4405* (2013.01); *A61B 8/485* (2013.01); *G06T 7/344* (2017.01); *G06T 11/008* (2013.01); *A61B 2090/374* (2016.02); *A61B 2090/3735* (2016.02); *G06T 2207/10072* (2013.01); *G06T 2207/10132* (2013.01); *G06T 2207/20221* (2013.01); *G06T 2207/30056* (2013.01)

(58) Field of Classification Search
CPC ..... A61B 8/5261; A61B 8/4405; A61B 8/485; A61B 6/5247; A61B 6/032; A61B 2090/374; A61B 2090/3735; G06T 7/344; G06T 11/008; G06T 2207/30056; G06T 2207/10072; G06T 2207/10132; G06T 2207/20221

See application file for complete search history.

(56) References Cited

U.S. PATENT DOCUMENTS

2013/0006036 A1* 1/2013 Raleigh ................ A61N 5/1049
600/1
2013/0044927 A1* 2/2013 Poole .................... G06T 7/0014
382/131

(Continued)

*Primary Examiner* — John Strege
(74) *Attorney, Agent, or Firm* — Sughrue Mion, PLLC

(57) ABSTRACT

The medical imaging apparatus includes a storage unit configured to store a patient adaptive object model in which a statistical object model related to transformation of an object caused by a periodic movement is applied to characteristics of the object of a target patient; an image obtainer configured to acquire a first image of the target patient; and an image fuser configured to transform a second image of the target patient based on differences between a shape of the object extracted from the patient adaptive object model and a shape of the object displayed on the first image.

24 Claims, 27 Drawing Sheets

EXTRACTION OF OBJECT IN
CERTAIN RESPIRATORY PHASE

EXTRACTION OF
TARGET OBJECT

CALCULATION OF
DIFFERENCES

(51) Int. Cl.
  *G06T 7/33* (2017.01)
  *A61B 90/00* (2016.01)

(56) References Cited

U.S. PATENT DOCUMENTS

| | | | |
|---|---|---|---|
| 2015/0139515 A1* | 5/2015 | Smith .................... | A61B 6/032 |
| | | | 382/131 |
| 2016/0203609 A1* | 7/2016 | Wang .................... | A61B 5/055 |
| | | | 382/131 |

* cited by examiner

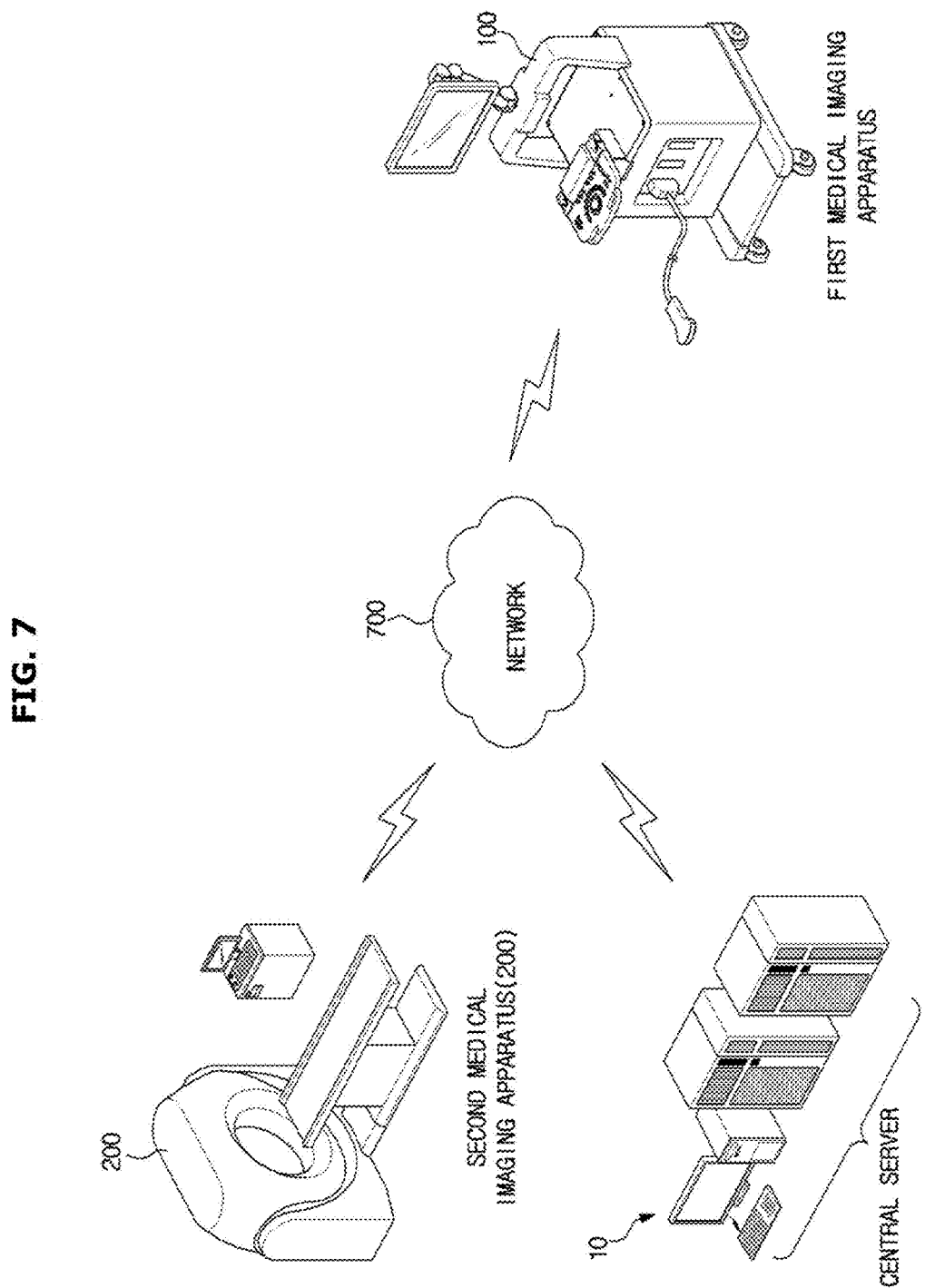

INSPIRATORY

EXPIRATORY

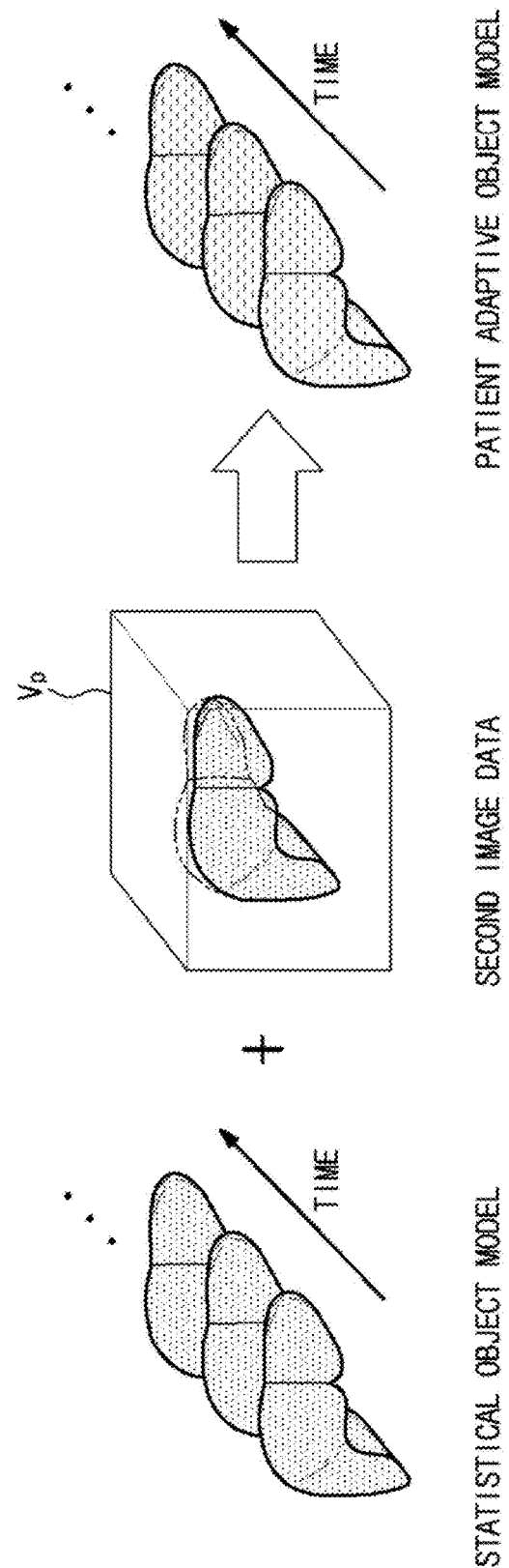

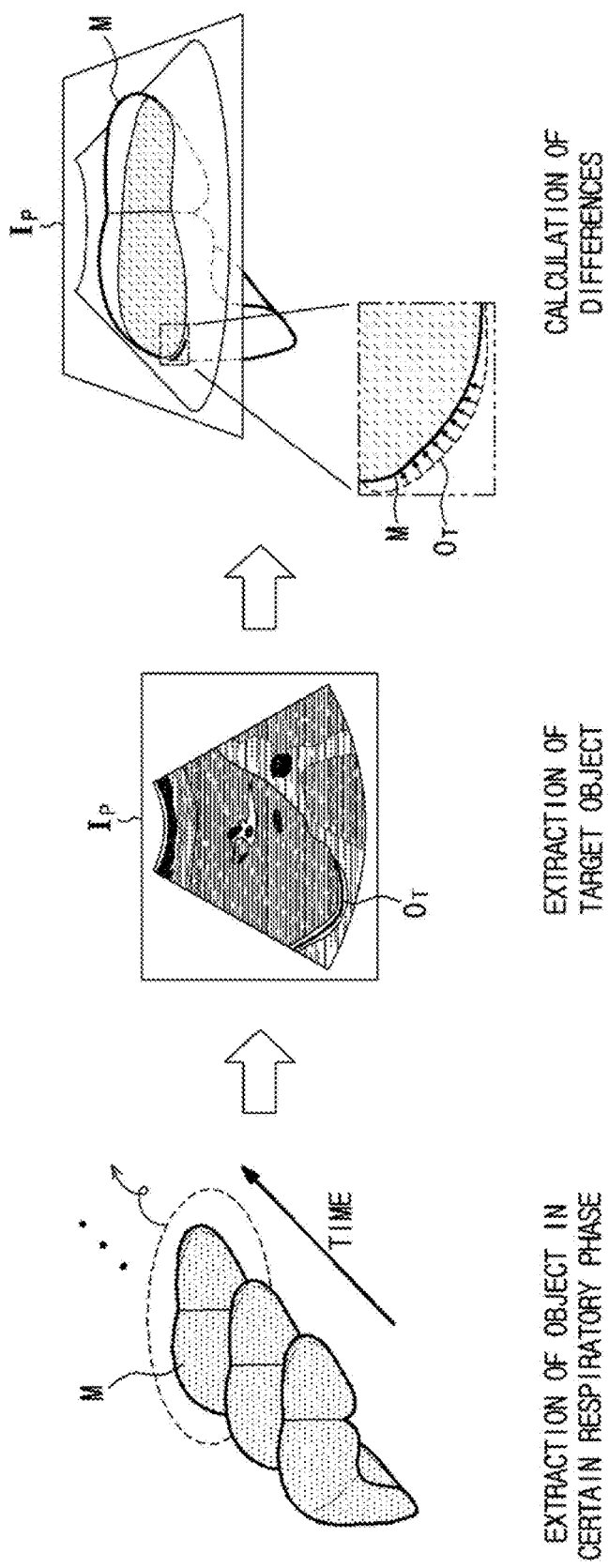

ESTIMATION OF FORCE DISTRIBUTION

IMAGE PROCESSING APPARATUS, MEDICAL IMAGE APPARATUS AND IMAGE FUSION METHOD FOR THE MEDICAL IMAGE

CROSS-REFERENCE TO RELATED APPLICATION

This application claims priority from Korean Patent Application No. 10-2014-0187456, filed on Dec. 23, 2014 in the Korean Intellectual Property Office, the disclosure of which is incorporated herein by reference in its entirety.

BACKGROUND

1. Field

Apparatuses and methods consistent with exemplary embodiments relate to image fusion, and, more particularly, to image registration of different modalities of images.

2. Description of Related Art

Medical imaging apparatuses acquire images of an object for the diagnosis or procedure. Examples of medical imaging apparatuses include radiography apparatuses, magnetic resonance imaging (MRI) apparatuses, mammography apparatuses, positron emission tomography (PET), computed tomography (CT) apparatuses, single photon emission computed tomography (SPECT) apparatuses, and optical coherence tomography (OCT) apparatuses.

Images acquired from the medical imaging apparatuses may have different characteristics, and the images of different imaging modalities may be combined so that the advantage of the images may be advanced and the disadvantages of the images may be compensated.

SUMMARY

One or more exemplary embodiments provide a medical imaging apparatus, an image processing apparatus, and an image fusion method for the medical image, which are configured to effectively and precisely correct a certain movement of the patient when performing image registration of different modalities of images.

In accordance with an aspect of an exemplary embodiment, a medical imaging apparatus includes a storage unit to store a patient adaptive object model in which a statistical object model related to transformation of an object caused by a movement of the patient is applied to the characteristics of the object of a target patient, and a second image of the target patient; an image obtainer to acquire a first image of the target patient; and an image fuser to transform the second image based on differences between a shape of an object extracted from the patient adaptive object model, and a shape of an object displayed on the first image.

The image fuser may estimate a boundary condition to correct the differences.

The image fuser may transform the patient adaptive object model by applying the boundary condition to a physical model to which the properties of the object of the target patient are applied.

The image fuser may generate the physical model based on the second image of the target patient and degree of elasticity of the object of the target patient.

The image fuser may transform the second image of the target patient by applying the transformation of the patient adaptive object model.

The image fuser may acquire a parameter of the movement probability distribution, which is related to which position each point of the object of the target patient is moved in a certain movement phase, and may generate the patient adaptive object model by applying the acquired parameter to the movement probability distribution of the statistical object model.

The image fuser may transform the 3D volume data by applying the transformation of the patient adaptive object model, and may extract a second image corresponding to a first image of the target patient from the transformed 3D volume data.

The image fuser may extract a second image corresponding to a first image of the target patient from the 3D volume data, and may transform the extracted second image by applying the transformation of the patient adaptive object model.

In accordance with an aspect of an exemplary embodiment, an image processing apparatus to fuse a first image and a second image, which have a different modality from each other, includes a storage unit to store a patient adaptive object model which is transformed statistical object model related to transformation of an object caused by a periodic movement of the patient to be appropriate for the characteristics of the object of the target patient; and an image fuser to transform the second image based on differences between a shape of an object extracted from the patient adaptive object model, and a shape of an object displayed on the first image.

In accordance with an aspect of an exemplary embodiment, an image fusion method to fuse a first image and a second image, which have a different modality from each other, includes storing a patient adaptive object model which is transformed statistical object model related to transformation of an object caused by a periodic movement of the patient to be appropriate for the characteristics of the object of the target patient; and transforming the second image of the target patient based on differences between a shape of an object extracted from the patient adaptive object model, and a shape of an object displayed on the first image.

BRIEF DESCRIPTION OF THE DRAWINGS

The above and/or other aspects will become more apparent by describing certain exemplary embodiments with reference to the accompanying drawings, in which:

FIG. 7 is a view schematically illustrating a process in which a medical imaging apparatus receives image data from a second medical imaging apparatus according to an exemplary embodiment;

FIG. 12 is a view schematically illustrating a process of generating a patient adaptive object model;

FIGS. 13, 14, 15, and 16 are views illustrating a process of correcting differences between a first image of the patient and a patient adaptive object model;

DETAILED DESCRIPTION

Figure 1:
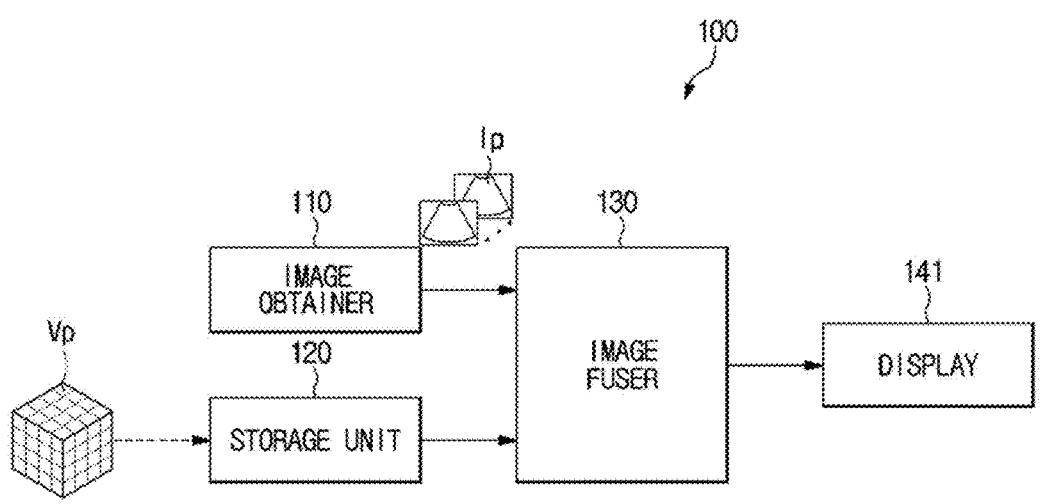
FIG. 1 is a control block diagram illustrating a medical imaging apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

Referring to FIG. 1, a medical imaging apparatus 100 according to an exemplary embodiment may include an image obtainer 110 to acquire a first medical image, a storage unit 120 to store second image data, an image fuser 130 to perform image registration between the first image and the second image and to correct a certain movement of the patient and a display 141 to display the first image, in which image registration is performed, and the second image.

The first image and the second image may represent images of different modalities. The different modalities of images may mean images having different principles of acquisition, images having different purposes of acquisition even having the same principles of acquisition, or images having different methods to display images.

For example, an ultrasound image may be acquired by emitting ultrasonic waves to an object and detecting echo ultrasonic waves reflected from the object. An X-ray image may be acquired by emitting X-rays to an object and detecting X-rays passed through the object. The ultrasound image and the X-ray image may be different modalities of images since image acquisition methods are different from each other.

Even when acquiring images of the object by using X-rays in the same manner, images may be the different modalities of images depending on the diagnosis and procedure purpose. For example, although the images acquired by the radiography such as a chest X-ray, an arm X-ray, a leg X-ray, etc., fluoroscopy acquiring video X-ray images, such as angiography, CT acquiring a tomographic image and a 3D image of the patient, tomosynthesis acquiring a tomographic image and a 3D image of breasts are images acquired by X-rays, the images may be different modalities of images.

A first image may be a two-dimensional (2D) image, or a three-dimensional (3D) image. In addition, when the first image is the 2D image, the first image may be a tomographic image or a projection image.

The second image may have different modality from the first image, but the second image may be an image having the same shape or the same dimension as the first image. For example, when the first image is a 2D cross-sectional image, the second image may be a 2D cross-sectional image, and when the first image is a 3D image, the second image may be a 3D image.

The second image may be an image having a different shape including at least one portion corresponding to the first image. For example, when the first image is a 2D cross-sectional image, the second image may be a 3D image including at least one portion corresponding to the first image, or a 2D projection image including at least one portion corresponding to the first image.

Second image data may represent image data including the second image, or 3D volume data $V_p$. However, exemplary embodiments of the medical imaging apparatus 100 are not limited thereto, the second image data may be 2D plane data.

The image obtainer 110 may include a scanner to scan an object to acquire the first image, and the configuration thereof may be various according to the type of the medical imaging apparatus 100.

An object may represent a specific part of the patient, which is a target to be scanned of the image obtainer 110, and the patient may be a human body or an animal.

The first image $I_p$ acquired by the image obtainer 110 may be transmitted to the image fuser 130 to be used for image registration with the second image and correcting a certain movement of the patient.

The storage unit 120 may store the second image data $V_p$ received from an external device, and the image fuser 130 may use the stored second image data $V_p$ to perform image registration with the first image $I_p$ and to correct a certain movement of the patient.

The medical imaging apparatus 100 acquiring the first image may correspond to a first medical imaging apparatus, and the second image data may be acquired by a second medical imaging apparatus, which is a different type of the first medical imaging apparatus 100.

The first medical imaging apparatus and the second medical imaging apparatus may be different from each other selected from a group including an ultrasound imaging apparatus, an OCT apparatus, an MRI apparatus, an X-ray imaging apparatus, a SPECT apparatus, and a PET apparatus. The X-ray imaging apparatus may include at least one of a tomography apparatus, a recording apparatus, and a mammography apparatus.

The first medical imaging apparatus may acquire video displaying a certain movement of the patient, and the video may be acquired in real time. The certain movement of the patient may represent a periodic movement with a constant pattern, such as respiration and heart rate of the patient, and the period of the certain movement may be constant or not.

The first medical imaging apparatus may be used for the purpose of simple diagnosis, and may be used for the procedure in invasive or non-invasive manner when acquiring the real-time video.

The first image and the second image, which have a different modality from each other, may be fused to be complementary. For example, when the first medical imaging apparatus is an ultrasound imaging apparatus, a relatively high spatial resolution image may be provided in real time. When the second medical imaging apparatus is an MRI apparatus, an image having excellent position resolution and soft tissue discrimination capability may be provided. Therefore, the first image acquired by the first medical imaging apparatus and the second image acquired by the second medical imaging apparatus having complementary characteristics to the first medical imaging apparatus may be fused to be applied to a variety of diagnosis or the procedure field.

Figure 2:
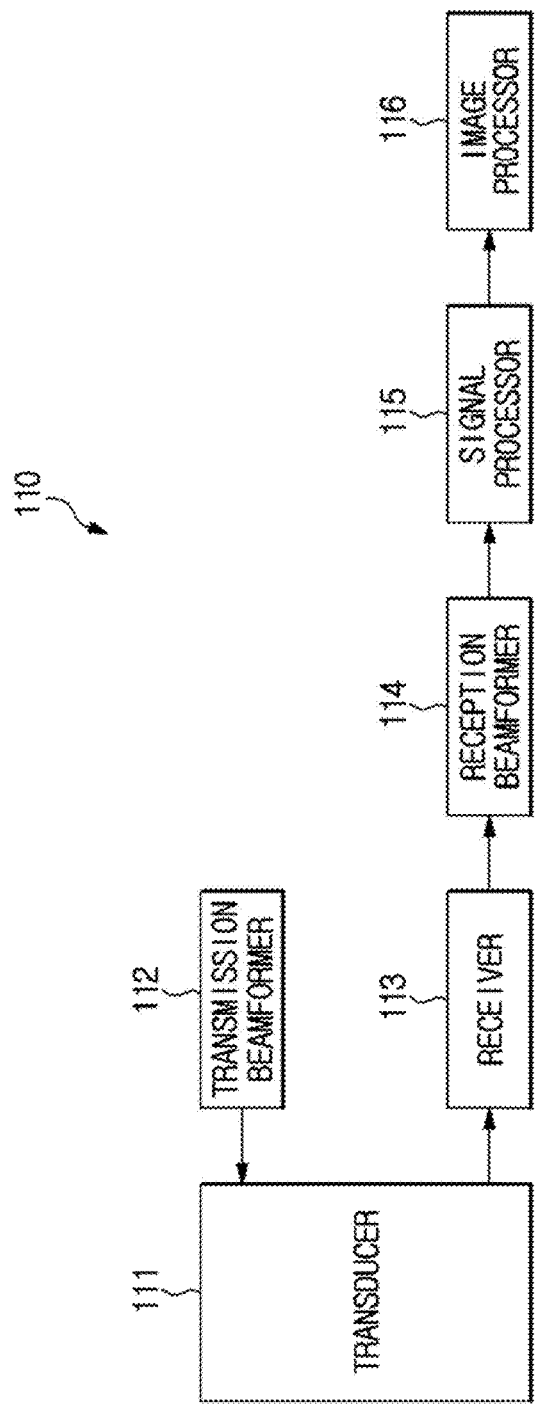
FIG. 2 is a control block diagram illustrating a configuration of an image obtainer when a medical imaging apparatus is an ultrasound imaging apparatus.

FIG. 2 is a control block diagram illustrating a configuration of an image obtainer when a medical imaging apparatus is an ultrasound imaging apparatus.

When the medical imaging apparatus 100 is an ultrasound imaging apparatus, as illustrated in FIG. 2, the image obtainer 110 may include a transducer 111 to convert an ultrasound signal into an electrical signal, a transmission beamformer 112 to perform beamforming on an ultrasound transmission signal, a receiver 113 to receive echo ultrasound signal, a reception beamformer 114 to perform beamforming on an echo ultrasound signal, a signal processor 115 to form ultrasound image data by performing signal processing on a digital signal converted from echo ultrasound signal, and an image processor 116 to perform various image processing to display ultrasound image data.

The transducer 111 may include a plurality of transducer elements, which convert an electrical signal into an ultrasound signal to transmit the ultrasound signal to an object, and convert an ultrasound signal reflected from the object into an electrical signal. The transducer element may include magnetostrictive ultrasonic transducers that convert wave energy into electric energy using the magnetostrictive effect of a magnetic material, piezoelectric ultrasonic transducers using the piezoelectric effect of a piezoelectric material, piezoelectric micromachined ultrasonic transducer (pMUT), or capacitive micromachined ultrasonic transducers (cMUT) that transmit and receive ultrasonic waves using vibration of several hundreds or thousands of micromachined thin films.

The transmission beamformer 112 may apply a time delay to a transmission signal having a predetermined frequency or a predetermined bandwidth, and the time-delayed transmission signal may be converted into an ultrasound signal in the transducer 111 and transmitted to the object. Due to the time delay applied to the transmission signal, the ultrasound transmission signal may be focused on a focal point placed inside the object, which makes a resolution of an image be improved.

An echo ultrasound signal reflected from the object reach the transducer 111 again, and the transducer 111 converts the echo ultrasound signal into an electrical signal.

An electrical signal converted from echo ultrasound signal may be input to the receiver 113. The receiver 113 may include a pre-amplifier to amplify analog reception signal. The pre-amplifier may include a low noise amplifier (LNA) or variable gain amplifier (VGA) (not shown) configured to control gain value according to an input signal. The VGA may employ time gain compensation (TGC) configured to compensate a gain according to a focal point or a distance from a focal point.

Echo ultrasound signal amplified in the receiver 113 may be input to the reception beamformer 114. The reception beamformer 114 may apply proper time delay to echo ultrasound signals, which reach the transducer with a time difference, to sum the echo ultrasound signals at the same time, and thus a Signal to Noise Ratio (SNR) may be improved.

The signal processor 115 may perform signal processing of a digital signal converted from the echo ultrasound signal. Analog to digital conversion of echo ultrasound signal may be performed on a front end or a rear end of the reception beamformer 114.

For example, the signal processor 115 may include a digital signal processor (DSP), and may generate ultrasound image data by performing envelope detection process configured to detect the size of echo ultrasound signal based on focused digital reception signal. Particularly, the signal processor 115 may generate ultrasound image data based on location information of multiple focal points existed on an each scan line, and based on data acquired from each point. The ultrasound image data may include a coordinate of each point in X-Y coordinate system, information related to each scan line angle about a vertical scan line, and data acquired from each point.

The image processor 116 may include a scan converter to perform scan conversion so that ultrasound image data may be displayed on the display 141. The image processor 116 may perform a variety of image processing of scan converted ultrasound image data to display an ultrasound image in a mode user desired on the display 141. For example, the image processor 116 may generate an ultrasound image in various modes, such as amplitude mode (A-mode), brightness mode (B-mode), motion mode (M-mode) or Doppler mode, to display on the display 141.

An ultrasound image generated by the image processor 116 may be input into the image fuser, and may be fused with the second image stored in the storage unit, and thus may be displayed on the display.

Figure 3:
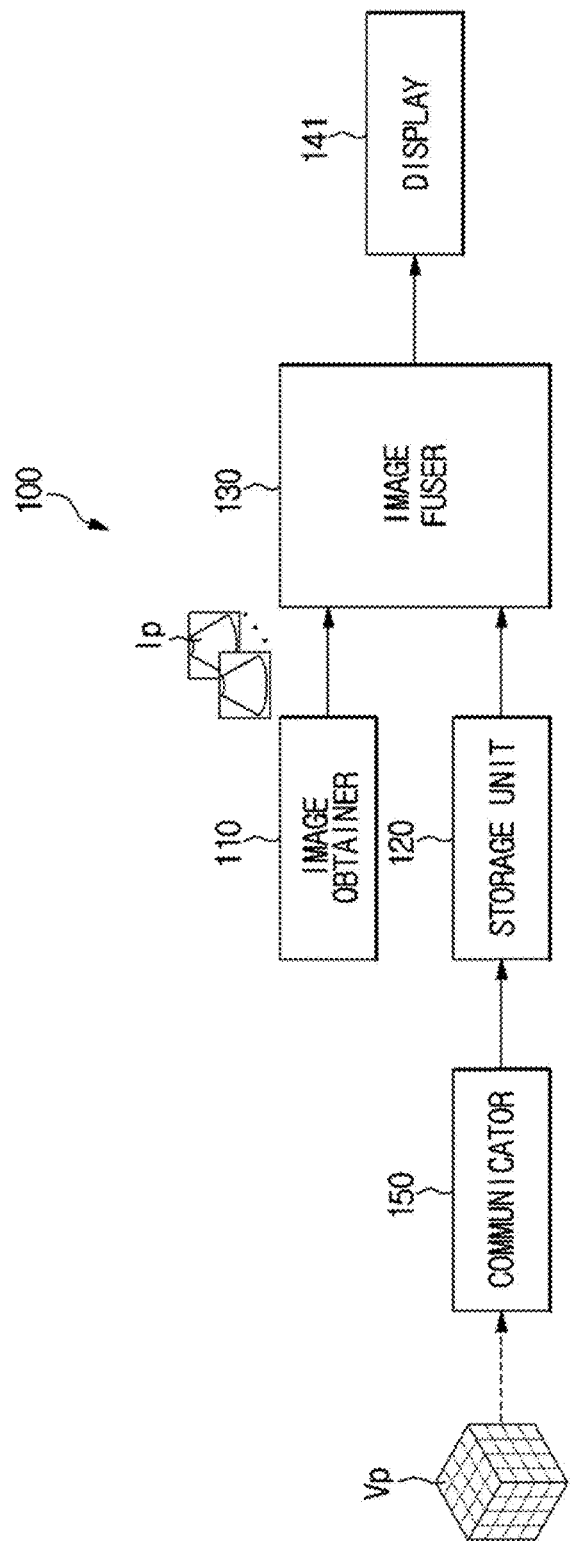
FIG. 3 is a control block diagram illustrating a medical imaging apparatus further including a communicator.

FIG. 3 is a control block diagram illustrating a medical imaging apparatus further including a communicator.

The storage unit 120 may include a storage medium, such as semiconductor memory, i.e., Read Access Memory (RAM), Read Only Memory (ROM), and flash memory, magnetic memory, such as magnetic disk, and optical disk, such as CD-ROM.

The second image data stored in the storage unit 120 may be transmitted to the second medical imaging apparatus via a communication network or a detachable storage medium, such as a USB memory.

When the second image data is transmitted via a communication network, as illustrated in FIG. 3, the medical imaging apparatus may further include a communicator 150. The communicator 150 may include at least one component, i.e., local area communication module, wired communication module, wireless communication module, to allow a communication with an external apparatus.

The local area communication module may represent a module to perform local area communication with an apparatus located within a certain distance. According to an exemplary embodiment, applicable local communication technologies may be Wireless LAN, Wi-Fi, Bluetooth, ZigBee, Wi-Fi Direct (WFD), ultra wideband (UWB), infrared Data Association (IrDA), Bluetooth Low Energy (BLE), Near Field Communication (NFC), but is not limited thereto.

The wired communication module may represent a module for a communication by using an electrical signal or an optical signal, and may include wired communication technologies by using a pair cable, a coaxial cable, and an optical fiber cable, but is not limited thereto. Other than the above, wired communication technologies known to those skilled in the art may be included.

The wireless communication module may include an antenna or a wireless communication chip to transmit/receive a wireless signal to/from at least one of a base station, an external apparatus, and a server on a mobile communication network. For example, the wireless communication may be a wireless communication module supporting Institute of Electrical and Electronics Engineers (IEEE802.11x) standards.

Figure 4:
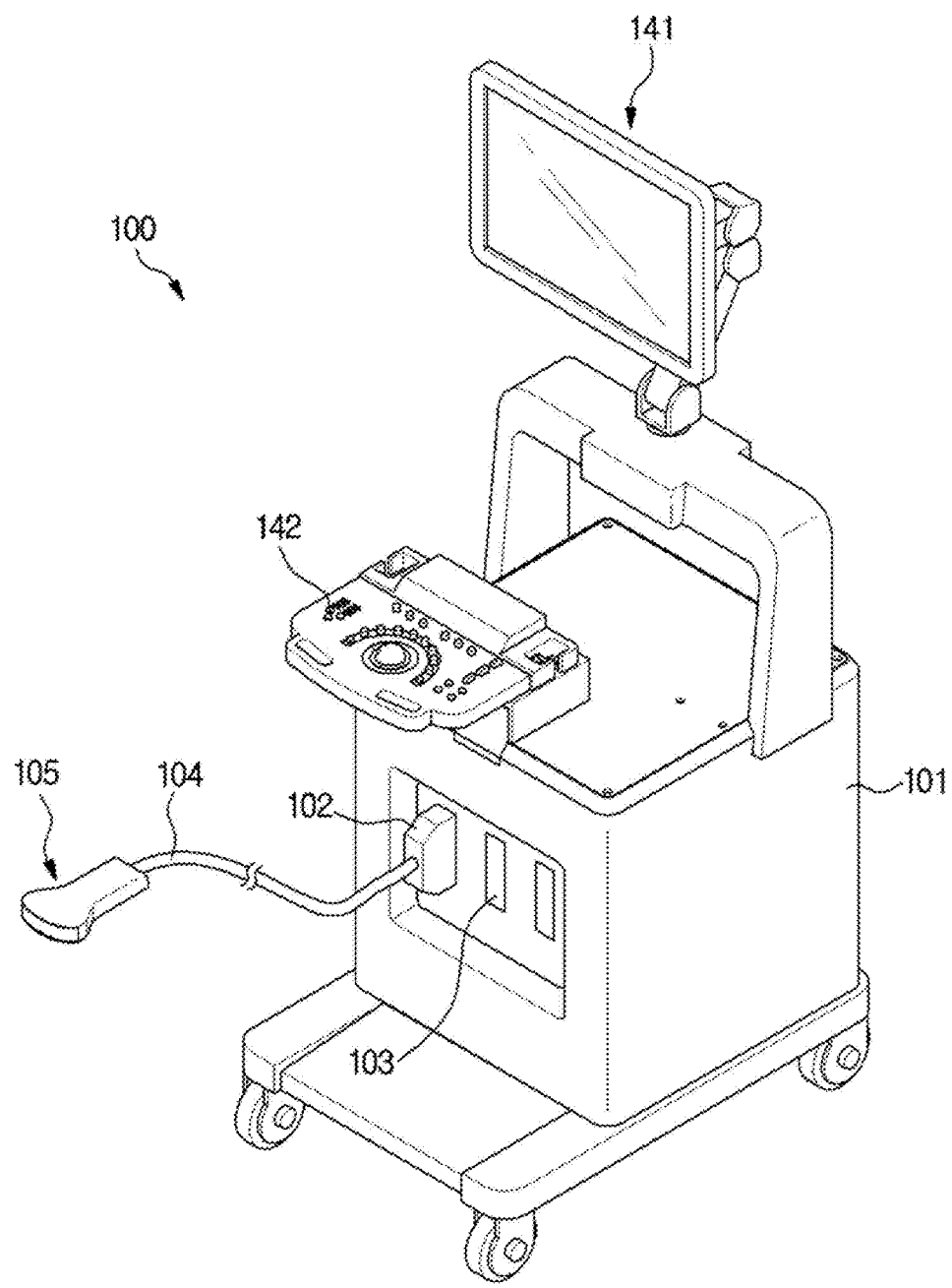
FIG. 4 is a view illustrating an ultrasound imaging apparatus.
Figure 5A:
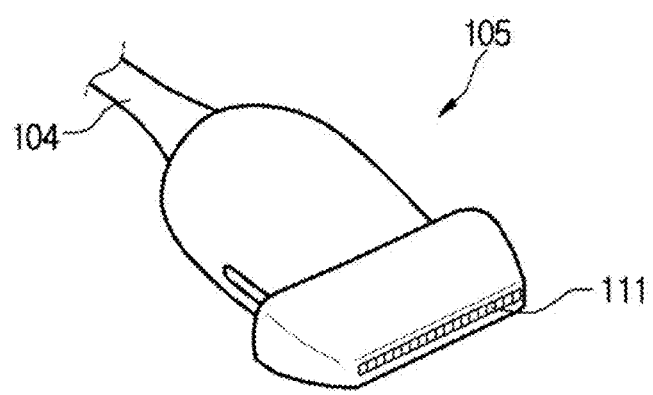
FIGS. 5A and 5B are views illustrating a probe included in an ultrasound imaging apparatus.
Figure 5B:
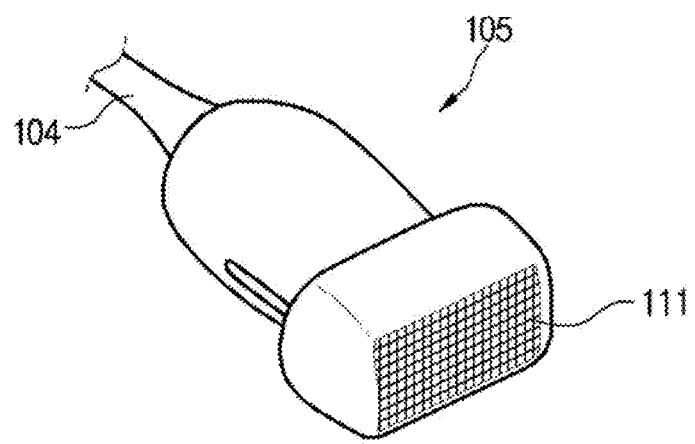

FIG. 4 is a view illustrating when a medical imaging apparatus is an ultrasound imaging apparatus and FIGS. 5A and 5B are views illustrating a probe included in an ultrasound imaging apparatus.

Referring to FIG. 4, a medical imaging apparatus 100 may include a body 101 provided with a display 141 and an input unit 142, and a probe 105 connected to the body 101.

Some components of an image obtainer 110 may be placed in the probe 105. For example, a transducer 111, a transmission beamformer 112, a receiver 113 and a reception beamformer 114 may be embedded in the probe 105, or the transducer 111 and the receiver 113 may be embedded in the probe 105 and the transmission beamformer 112 and the reception beamformer 114 may be embedded in the body 101. As long as the transducer 111 is embedded in the probe 105, the physical location of the remaining components is not limited.

The probe 105 may be connected to the body 101 through a cable 104. One side end of the cable 104 may be connected to the probe 105 and a connector 102 attachable or detachable to a slot 103 of the body 101 may be provided in the other side end of the cable 104. By using the cable 104, a control command and data may be exchanged between the body 101 and the probe 105. Alternatively, when the probe 105 is a wireless probe, the probe 105 may be connected to the body 101 through a wireless network.

The transducer 111 may include a plurality of transducer elements. The plurality of transducer elements, as illustrated in FIG. 5A, may be arranged in a linear manner, or in a convex manner. When arranged in a convex manner, ultrasound beam emitted from the probe 105 may have a fan shape so that the generated ultrasound image may have a fan shape.

A transducer element illustrated in FIG. 5A, may be arranged in one dimension, but may be arranged in two dimensions, as illustrated in FIG. 5B. When the transducer element is arranged in two dimensions, a 3D image of an object may be acquired.

Referring to FIG. 4 again, the display 141 may be provided to display an ultrasound image, an image in which an ultrasound image and other modality of image are fused, or a screen configured to receive an input of a control command.

The display 141 may include at least one of Liquid Crystal Display (LCD), Light Emission Diode (LED) display, Plasma Display Panel (PDP) display, and Organic Light Emission Diode (OLED) display.

FIG. 4 illustrates that the display 141 is configured with a single screen, but is not limited thereto. The display 141 may be configured with a plurality of screens.

An input unit 142 configured to receive an input of a control command from a user may be provided in the body 101. The input unit 142 may be at least one of jog shuttle, track ball, button, mouse, key board, and touch panel.

Figure 6A:
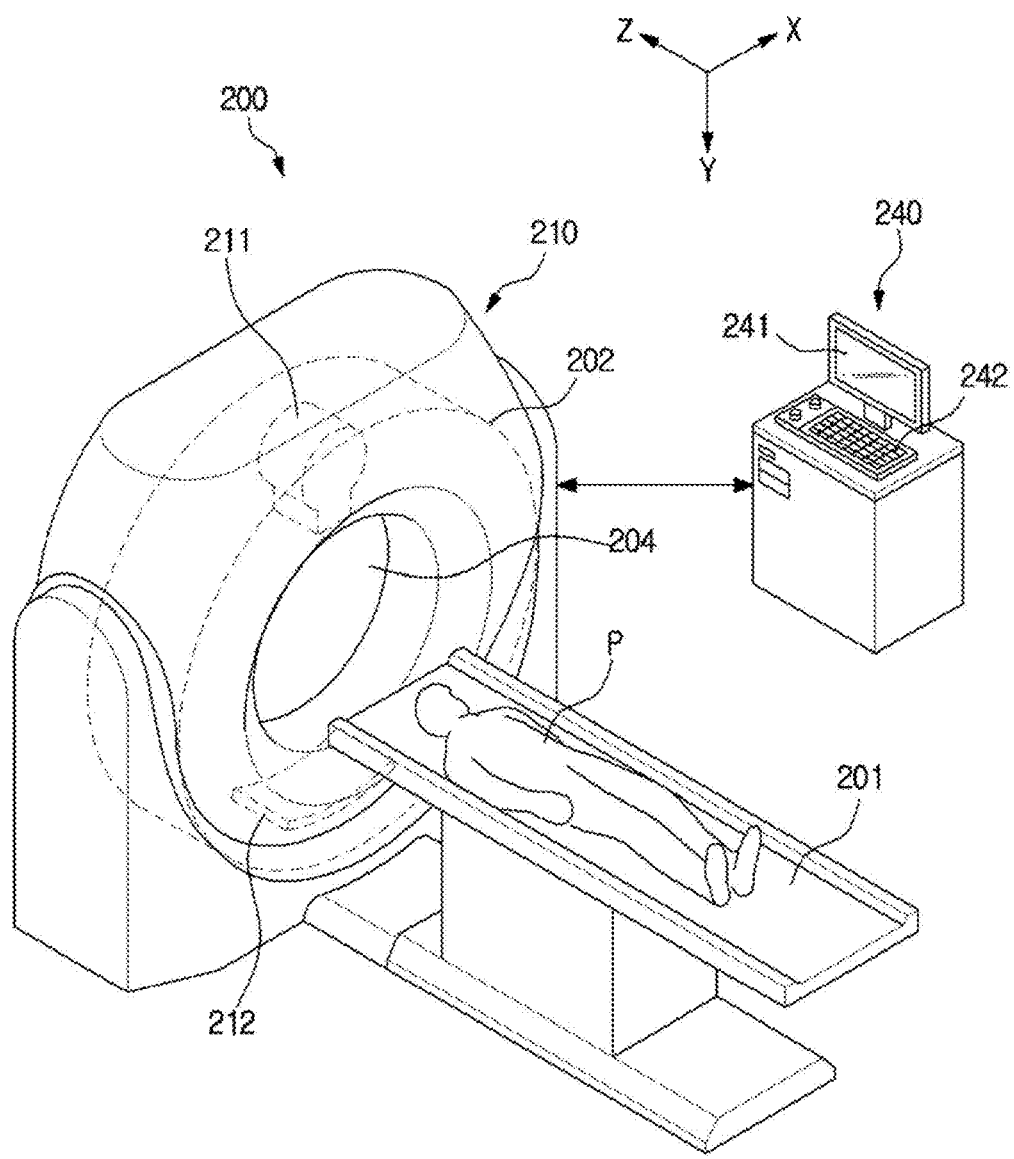
FIG. 6A is a view illustrating a CT apparatus.
Figure 6B:
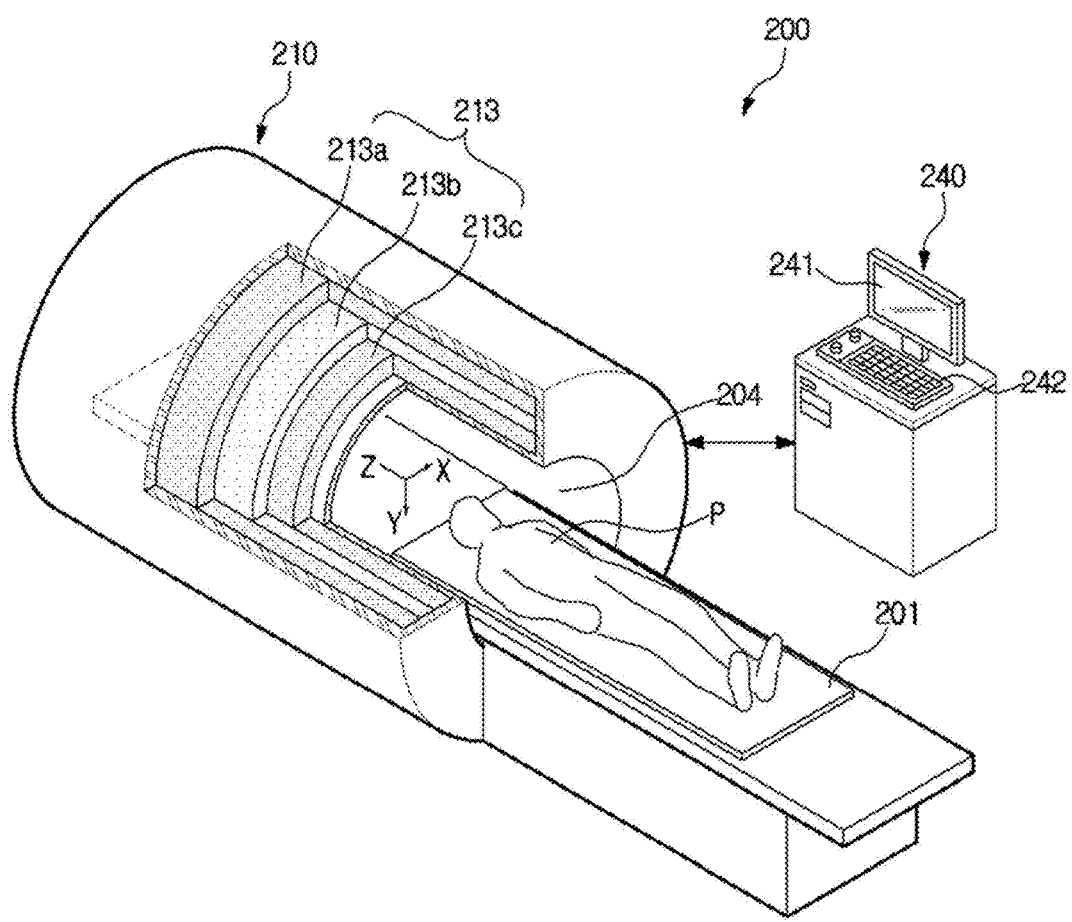
FIG. 6B is a view illustrating an MRI apparatus.
Figure 6C:
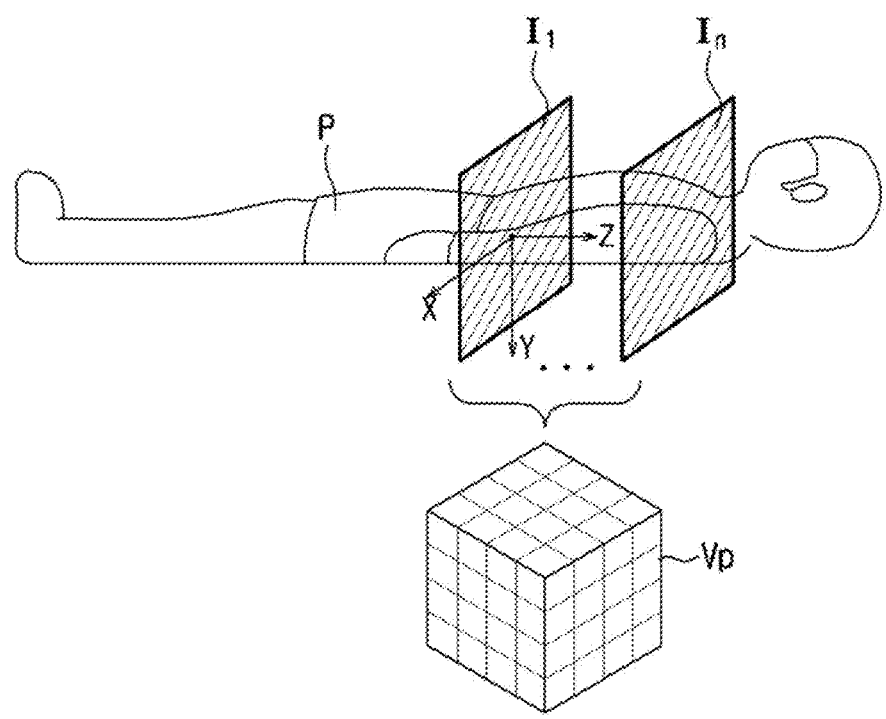
FIG. 6C is a view schematically illustrating information included in second image data.

FIG. 6A is a view illustrating a second medical imaging apparatus which is a CT apparatus, FIG. 6B is a view illustrating a second medical imaging apparatus which is an MRI apparatus, and FIG. 6C is a view schematically illustrating information included in a second image data.

As illustrated in FIG. 6A, a second medical imaging apparatus may be a CT apparatus. The second imaging apparatus may include an image obtainer 210 to acquire a second image, an X-ray source 211 to emit X-rays to an object by generating X-rays, and an X-ray detector 212 to detect X-rays passed through the object.

The X-ray source 211 and the X-ray detector 212 are mounted to a gantry 202 while facing each other. When a patient table 201 delivers a patient P into a bore 204, the gantry 202 may scan the patient P to acquire projection data while rotating around the bore 204.

The second imaging apparatus 200 may include a workstation 240 to provide a user interface, and to perform various processing related to projection data.

The workstation 240 may include a display 241 to display generated images and an input unit 242 to receive an input of a control command from a user. The display 241 and the input unit 242 may be the same as the display 141 and the input unit 142 of the first medical imaging apparatus 100.

Although not shown, the second medical imaging apparatus 200 may further include an image processor configured to generate a cross-sectional image by reconstructing projection data acquired by the image obtainer 210, and configured to generate 3D volume data of the object by stacking a plurality of cross-sectional images, and the image processor may be provided in the workstation 240.

As illustrated in FIG. 6B, a second medical imaging apparatus may be an MRI apparatus. The image obtainer 210 may include a magnet assembly 213 surrounding a bore 204, and may include a main magnet 213a to form a static magnetic field, a gradient coil 213b to form a gradient magnetic field by applying gradient to the static magnetic field, and an RF coil 213c to excite an atomic nuclei by applying RF pulses to an object, and to receive echo signal from these atomic nuclei.

When a patient table 201 is transferred into the bore 204 in which a static magnetic field is formed, atomic nuclei constituting the patient may be excited by applying a gradient magnetic field and RF pulses to generate an echo signal so that the object may be imaged by receiving the echo signal.

The image processor provided in the workstation 240 may generate a cross-sectional image of the object by reconstructing the echo signal, and may generate 3D volume data by stacking a plurality of cross-sectional images.

Referring to FIG. 6C, when a scan is performed in a state where a longitudinal axis of the patient is parallel to a Z-axis, the image processor may generate a cross-sectional image perpendicular to the Z-axis by reconstructing data related to X-rays detected by the X-ray detector 212 or by reconstructing data related to echo signal received by the RF coil 213c.

The image processor may generate a plurality of cross-sectional images $I_1$ to $I_n$ (n is an integer of 2 or more) in a longitudinal axis of the patient P, and may generate 3D volume data $V_p$ of a certain region of the patient P by stacking the plurality of cross-sectional images. The 3D volume data $V_p$ may include voxels having scalar values or vector values both of which are sampled in a certain interval.

The 3D volume data $V_p$ of the patient P may be transmitted to other apparatus in the outside through a communicator provided in the second medical imaging apparatus 200 or a storage medium, such as a USB. The communicator provided in the second medical imaging apparatus 200 may include at least one component, such as local area communication module, wired communication module, and wireless communication module, to allow a communication with an external apparatus. The communication modules may be the same as in the communicator 150 of the first medical imaging apparatus 100, and thus a duplicate description will be omitted.

FIG. 7 is a view schematically illustrating a process in which a medical imaging apparatus receives image data from a second medical imaging apparatus according to an exemplary embodiment.

Referring to FIG. 7, 3D volume data $V_p$ of a certain region R of the patient P may be acquired by using the second medical imaging apparatus 200. The 3D volume data $V_p$ becomes a second image data transmitted to the first medical imaging apparatus 100.

A communicator of the second medical imaging apparatus 200 may be able to directly transmit the second image data to the first medical imaging apparatus 100 via a network 700, or may be able to transmit to a central server 10 configured to integrally manage images acquired by the first medical imaging apparatus 100 and the second medical imaging apparatus 200.

The central server 10 may be implemented by Picture Archiving Communication System (PACS). The images acquired by the first medical imaging apparatus 100 and the second medical imaging apparatus 200 and the images, which are acquired by other medical imaging apparatuses located in an institution where the first medical imaging apparatus 100 and the second medical imaging apparatus 200 are located, may be transmitted to the central server 10 to be managed.

The central server 10 may receive and store the second image data from the second medical imaging apparatus 200, and may transmit the stored second image data to the first medical imaging apparatus 100 as needed. For example, when the first medical imaging apparatus 100 requests second image data of a certain patient from the central server 10, the central server 10 may transmit the second image data to the first medical imaging apparatus 100.

The communicator 150 of the first medical imaging apparatus 100 may receive the second image data from the central server 10, and may store the second image data in the storage unit 120. When a first image of the patient is acquired, the image fuser 130 may fuse the acquired first image and the stored second image. The second image data received by the first medical imaging apparatus 100 is about the patient P who is intended to be scanned in real time, and, to distinguish from a general patient, a patient who is currently scanned in the first medical imaging apparatus, will be referred to as "a target patient."

There may be differences between acquisition time of the first image of the target patient and acquisition time of the second image of the target patient. For example, the first image may be acquired after several days or several hours have been passed from when the second image data is acquired. So long as the second image data is acquired before the first image is acquired, a particular acquisition time is not limiting.

The first medical imaging apparatus 100 may be applied to the interventional procedure to perform the procedure by using images. The interventional procedure is a treatment method for performing diagnosis and treatment by using the medical imaging apparatus as a guidance device. Radiofrequency ablation (RFA) and High-Intensity Focused Ultrasound (HIFU) are particular examples of the procedure. The RFA is a treatment in which an electrode is inserted into the lesion to generate high-frequency, and thus the lesion is burned and removed by heat by the high-frequency. The RFA may be effectively used to remove cancer cells in the liver. The HIFU is a treatment in which the lesion cells are caused to die by selective coagulation necrosis by focusing ultrasonic waves having high-intensity on a point. When performing these treatments, the lesion needs to be accurately distinguished from normal tissues in the surrounding tissue, and thus an image providing structural information and anatomical information in the body may be selected as the second image to be used to be complementary with the first image.

Particularly, when the first medical imaging apparatus 100 is an ultrasound imaging apparatus, and the second medical imaging apparatus 200 is a CT apparatus, the RFA may be performed. In this case, 3D volume data of the liver of the target patient may be acquired in advance by using the second imaging apparatus 200. The communicator 150 of the first imaging apparatus 100 receives the 3D volume data acquired by the second imaging apparatus 200, and the image obtainer 110 acquires an ultrasound image of the liver of the target patient in real time.

The display 141 may display an ultrasound image acquired in real time and a user may perform the procedure while confirming the displayed ultrasound image in real time. Here, when a tomographic image corresponding to an ultrasound image of the target patient, which is extracted from pre-stored 3D volume data, is displayed with a real-time ultrasound image, the accuracy of the procedure may be improved.

A patient has a certain movement, such as respiration and heartbeat, and thus the internal organs of the patient including the liver may be transformed caused by those movements. Therefore, when fusing the first image and the second image, the image fuser 130 may transform the second image by reflecting a certain movement of the patient.

Figure 8:
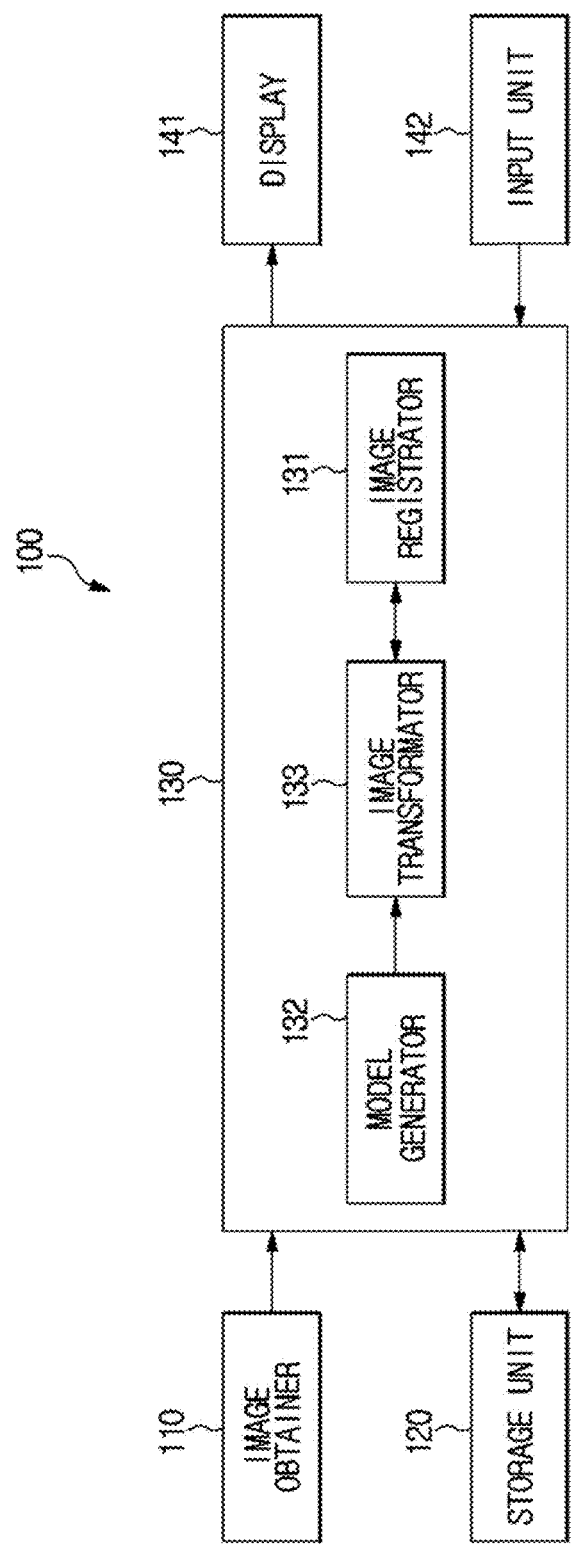
FIG. 8 a control block diagram illustrating an example of a configuration of an image fuser.

FIG. 8 a control block diagram illustrating an example of a configuration of an image fuser.

Referring to FIG. 8, the image fuser 130 may include an image registrator 131 to perform image registration between the first image and the second image, a model generator 132 to generate an adaptive object model indicating transformation of an object caused by a certain movement of the patient, an image transformator 133 to transform the second image of the patient by applying the transformation of an object caused by the certain movement of the patient.

The image fuser may include a memory to store programs and data to perform operations of various components, and a processor to process data according to the programs stored in the memory. Each component included in the image fuser may be implemented by a separate processor, or two or more components may share a processor. In addition, one or more processors may be shared with other components of a medical imaging apparatus other than the image fuser.

To display the first image along with the second image in which the first image and the second image are related to an area corresponding to each other, the image registrator may search the second image corresponding to the first image, and may perform image registration to match the position of the first image and the second image. Various image registration methods, such as a method performed manually in which a user designates a point or a side which is corresponding in the two images, and a method in which an ultrasound probe is located at a standard point, which is easily found, such as a solar plexus of a patient, a point corresponding to the standard point is automatically searched in the second image, and thus image registration is performed, may be applied to the image registration method. However, in exemplary embodiments, any image registration method known to those skilled in the art may be applied.

The image registration between the first image and the second image may be performed before or after applying transformation of an object caused by the certain movement of the patient to the second image.

The certain movement of the patient may represent a periodic movement, such as respiration or heartbeat, and a case where a certain movement of the patient is a respiration is described in detail below as an example.

Figure 9:
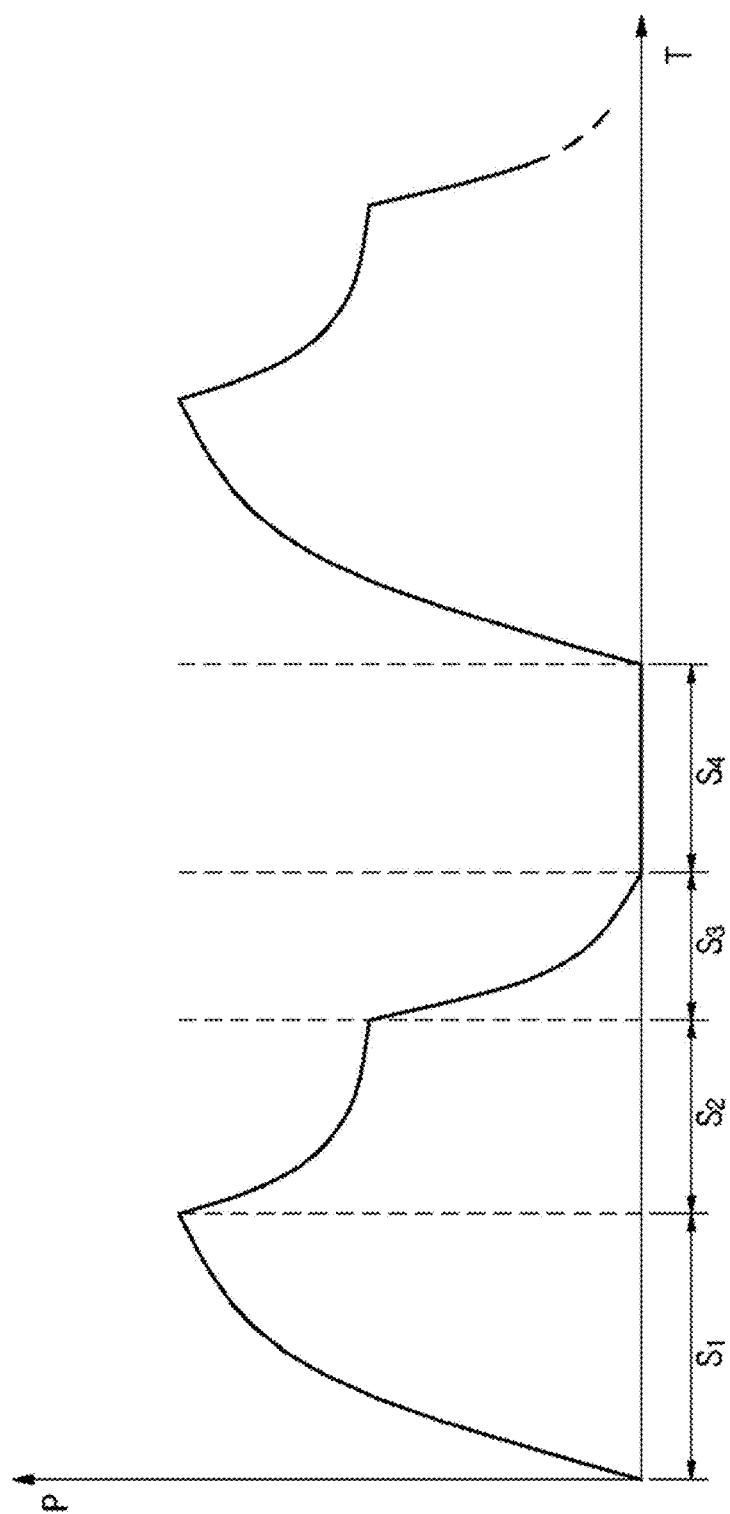
FIG. 9 is a graph illustrating respiratory phases and relative air pressures in each phase.

FIG. 9 is a graph illustrating respiratory phases and relative air pressures in each phase.

Referring to FIG. 9, the respiratory phase may be divided into inspiratory flow ($S_1$), inspiratory pause ($S_2$), expiratory flow ($S_3$), and expiratory pause ($S_4$). The respiratory phase may be determined by the action of the lungs and the diaphragm placed under the lungs. Particularly, when the diaphragm is lowered, the space surrounding the lungs is expanded, the pulmonary pressure is lowered and then the air is introduced from the outside to return the pulmonary pressure. Conversely, when the diaphragm is increased, the space surrounding the lungs is reduced, the pulmonary pressure is increased and then the air is discharged to the outside to return the pulmonary pressure. The inspiratory flow ($S_1$) is a term in which air is introduced to the lungs, and the inspiratory pause ($S_2$) is a term in which air is not introduced to the lungs any more but the expiratory flow is not started yet. The expiratory flow ($S_3$) is a term in which air is discharged from the lungs to the outside, and the expiratory pause ($S_4$) is a term in which air is not discharged from the lungs any more but the inspiratory flow is not started yet. These four phases may correspond to a single respiratory cycle.

Since the position of the costal bone and the diaphragm may be changed at each respiratory phase, the respiration may affect the shape and the position of other organs. For example, since the liver is placed just under the diaphragm, the shape of the liver may be transformed depending on the movement of the diaphragm.

Figure 10A:
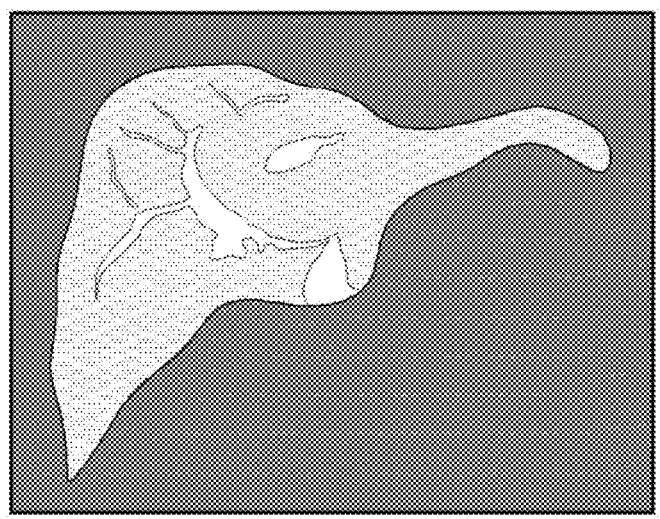
FIGS. 10A and 10B are views illustrating transformation of organs according to respiration.
Figure 10B:
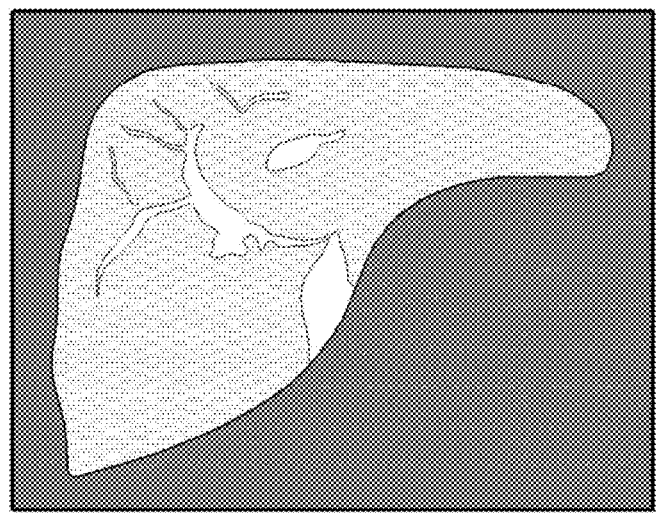

Referring to FIG. 10A, in the inspiratory flow, the diaphragm is lowered and the liver is pressed and thereby the shape of the liver is relatively flatter than the liver of the expiratory flow. Referring to FIG. 10B, in the expiratory flow, the diaphragm is increased and thereby the shape of the liver is relatively expanded as compared to that of the inspiratory flow.

When the first image is acquired in real time, a patient may be in easy respiration, and thus the transformation of the organ may be generated according to each respiratory phase. The medical imaging apparatus according to an exemplary embodiment may apply the transformation of the object caused by the respiration to the second image to precisely perform image registration between the first image and the second image. For this, the patient adaptive object model is generated by using statistical object model and the second image is transformed based on the patient adaptive object model.

The object may include a variety of organs, such as the liver, the lungs, the cardiac, and the kidneys, and may be different according to the diagnostic or treatment purposes. For example, when the RFA is performed by an ultrasound imaging apparatus, the liver may be the object. However, the liver might not be the only object displayed in correspondence to the field of view (FOV) in the first image and/or the second image. Therefore, an object that the user desires to observe that is adjacent to the object of interest of interest, e.g., liver, may also be displayed along with the liver in the first image and/or the second image. This case is described below in more detail with reference to FIG. 13.

Figure 11A:
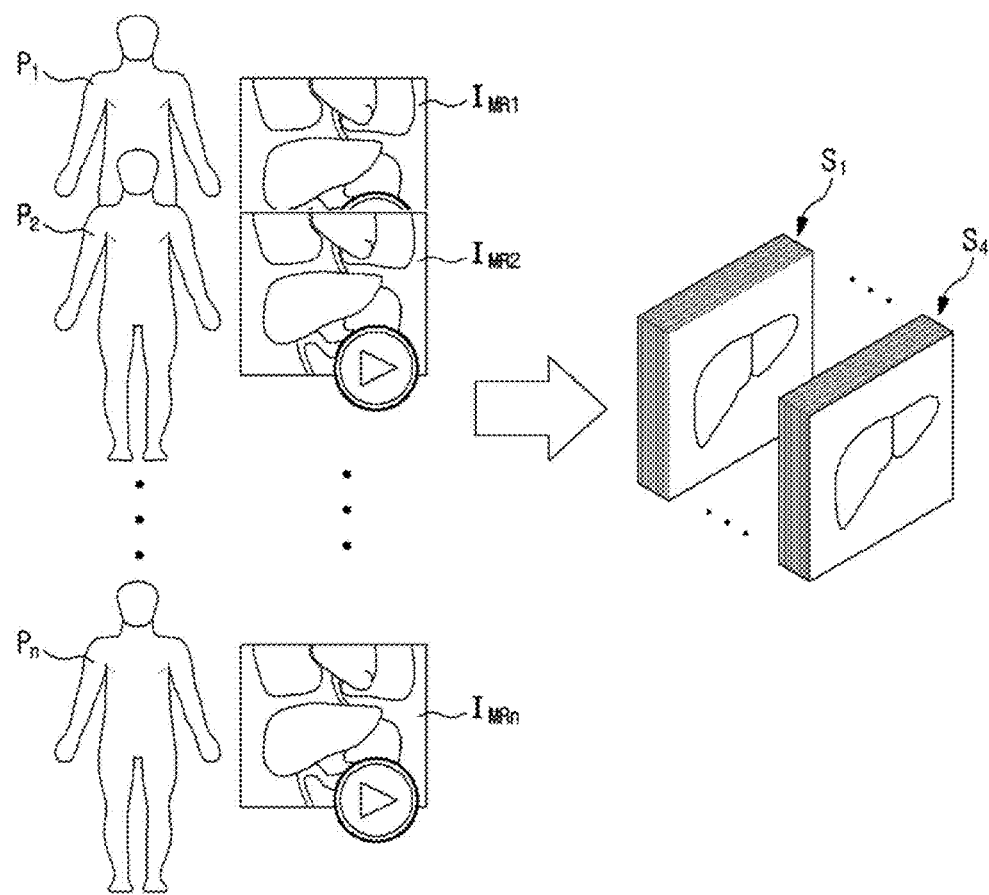
FIGS. 11A and 11B are views schematically illustrating a process of generating a statistical object model.
Figure 11B:
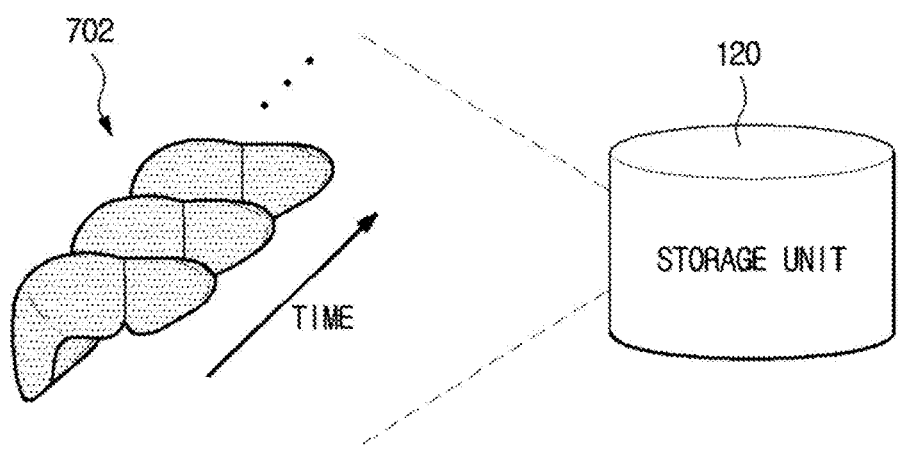

Referring to FIGS. 8, 11A, and 11B, the model generator may generate a patient adaptive object model by applying a statistical object model indicating the transformation of object caused by the respiration, to the second image data. The statistical object model may be stored in the storage unit in advance. Here, "stored in advance" may represent being stored before image registration between the first image and the second image, and the transformation of the second image, but a point time when the statistical object model is stored is not limiting.

The statistical object model may be generated by building a standard model related to the shape of the organs and the changes of position by acquiring the statistical distribution of changes in positions corresponding to each location of organs from four-dimensional (4D) MRI images taken from a number of patients. However, this is not limiting, and, for example, a video of the volume of an object and other types of images may be used.

Referring to FIG. 11A, through reconstructing and resampling of the images acquired in each of the respiratory phases $S_1$ to $S_4$ extracted from the 4D MRI images $I_{MR1}$ and $I_{MR2}$ to $I_{MRn}$ taken from first patient $P_1$ and second patient $P_2$ to Nth patient $P_n$ (n is an integer of 3 or more), the correspondence between the organs in a patient may be acquired.

With the probability distribution, the information about a position to which each point of the organ is moved to in the next respiratory phase, is acquired, and, thus, the probability distribution may be a statistical object model of a certain organ. The statistical object model 702 may be stored in the storage unit 120, as illustrated in FIG. 11B. FIGS. 11A and 11B illustrate the statistical object model of the liver, but the statistical object model, in which the respiratory effect is applied to other organs other than the liver, may be built and stored.

The statistical object model stored in the storage unit may be directly built in the model generator, or may be built in other external devices and may be transmitted to a medical imaging apparatus.

The model generator may generate a patient adaptive object model, which is modified for a target patient, by using a statistical object model stored in the storage unit 120 without a 4D medical image of the target patient.

FIG. 12 is a view schematically illustrating a process of generating a patient adaptive object model.

A model generator may generate a patient adaptive object model by using a statistical object model and a second image data of a target patient. The statistical object model stored in the storage unit is acquired from other patients and not a target patient, and, to compensate for this, the model generator may generate a patient adaptive object model including information, which is related to how an object of a target patient is transformed according to the respiratory phase, by applying a second image data $V_p$ of the target patient to the statistical object model, as illustrated in FIG. 12. Particularly, the model generator may acquire a parameter of the movement probability distribution, which is related to which position each point of the organ of the target patient is moved to in a certain respiratory phase, and may acquire a patient adaptive object model by applying the acquired parameter to the movement probability distribution of the statistical object model. The generated patient adaptive object model may be stored in the storage unit.

Data, such as second image data, a statistical object model, and a patient adaptive object model, stored in the storage unit may be stored temporarily or non-temporarily.

FIGS. 13 to 16 are views illustrating a process of correcting differences between a first image of the patient and a patient adaptive object model. In exemplary embodiments, a first image is an ultrasound image, an object is the liver, and a movement is respiration, however, this is a non-limiting example. For example, the movement may be caused by a heartbeat, the phases may correspond to cardiac phases, and the measurement may be performed by the ECG.

The physical properties of the organ may vary depending to the health condition of the target patient, and when there are differences between the condition of the organ of the target patient and the statistical object model, the accuracy of image registration may be compromised. The image transformator may modify a second image by correcting the difference between a first image of the target patient acquired in real time and a patient adaptive object model, by applying the physical properties of the organ of the target patient.

As illustrated in FIG. 13, the image transformator may extract the shape of the liver M corresponding to the present respiratory phase of the target patient from the patient adaptive object model. The respiration of the patient may be measured by using respiratory measurement apparatuses, such as optical tracker, respiratory belt, and spirometer. However, exemplary embodiments are not limited thereto, and any other appropriate method of measuring the respiration of the patient may be applied.

The image transformator may detect a target object $O_T$ from an ultrasound image of a patient, which is to be compared with the shape of the liver M extracted from the patient adaptive object model. When the liver is clearly displayed on the first image, the extracted shape of the liver may be directly compared with the liver displayed on the first image. However, since the boundary of the liver is not clear in the ultrasound image $I_P$, other organ, which is clearly displayed on the ultrasound image to be replaceable with the shape of the liver, may be extracted. For example, the diaphragm placed just over the liver may be detected as a target object $O_T$.

The image transformator may calculate differences between the shape of the liver extracted from the patient adaptive object model and the diaphragm detected from the ultrasound image. The calculation of the difference may include calculating a distance between the boundary of the liver extracted from the patient adaptive object model and the boundary of the diaphragm detected from the ultrasound image, and calculating differences between the positions thereof.

The image transformator may estimate a boundary condition to correct the calculated differences. For example, the boundary condition may be a force f. The force may be calculated by using a relation between a potential function and the force, or by using a distance between the boundary of the liver extracted from the patient adaptive object model and the boundary of the diaphragm detected from the ultrasound image, and the elastic coefficient. However, exemplary embodiments are not limited thereto, and other mathematical modeling or mathematical algorism known to those skilled in the art may be used to estimate a boundary condition for the correction of the differences.

The image transformator may transform the second image of the target patient by using the estimated force. A physical model to which the physical properties of the liver of the target patient are applied may be used. In the exemplary embodiments, since the image transformator may transform the image by applying the physical model to which the physical properties of the liver of the target patient are applied, image registration with high-definition may be performed although the condition of the organs of the patient is different from the statistical object model.

Particularly, the image transformator may generate the physical model from the shape of the organs extracted from the second image data, and the physical model may be based on a degree of elasticity of the organs. The degree of elasticity of the organs may be acquired by using ultrasound elastography or may be directly set based on clinical experience and medical knowledge of a user, such as a doctor.

The physical model to which the physical properties of the liver of the target patient are applied may be expressed by the following equation 1:

$$M\ddot{q}+D\dot{q}+Kq=f$$

Here, f is vector indicating force, and q, $\dot{q}$ and $\ddot{q}$ are vectors indicating displacement, velocity and acceleration, respectively. M, D and K represent matrix of mass, damping and stiffness. Since the values of M, D and K are known, q, $\dot{q}$ and $\ddot{q}$ may be calculated when f applied to the organ is known.

Figure 14:
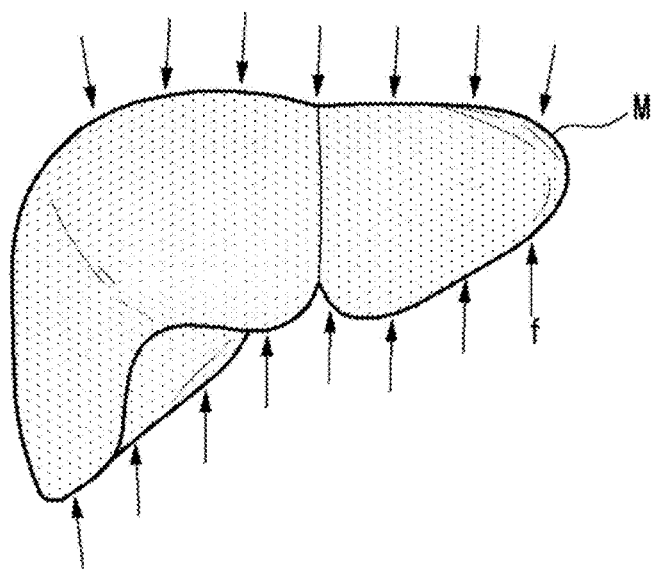

Therefore, when the estimated force is applied to equation 1, q, $\dot{q}$ and $\ddot{q}$ may be calculated. That is, as illustrated in FIG. 14, the distribution of the force, which is applied to all over the liver of the target patient, may be estimated, and q, $\dot{q}$ and $\ddot{q}$ each point of the entirety of the liver may be estimated. In other words, by applying the estimated force to the patient adaptive object model, the physical properties of the organ of the target patient are applied and the patient adaptive object model may be transformed. That is, the transformation of the organ may be estimated.

Figure 15:
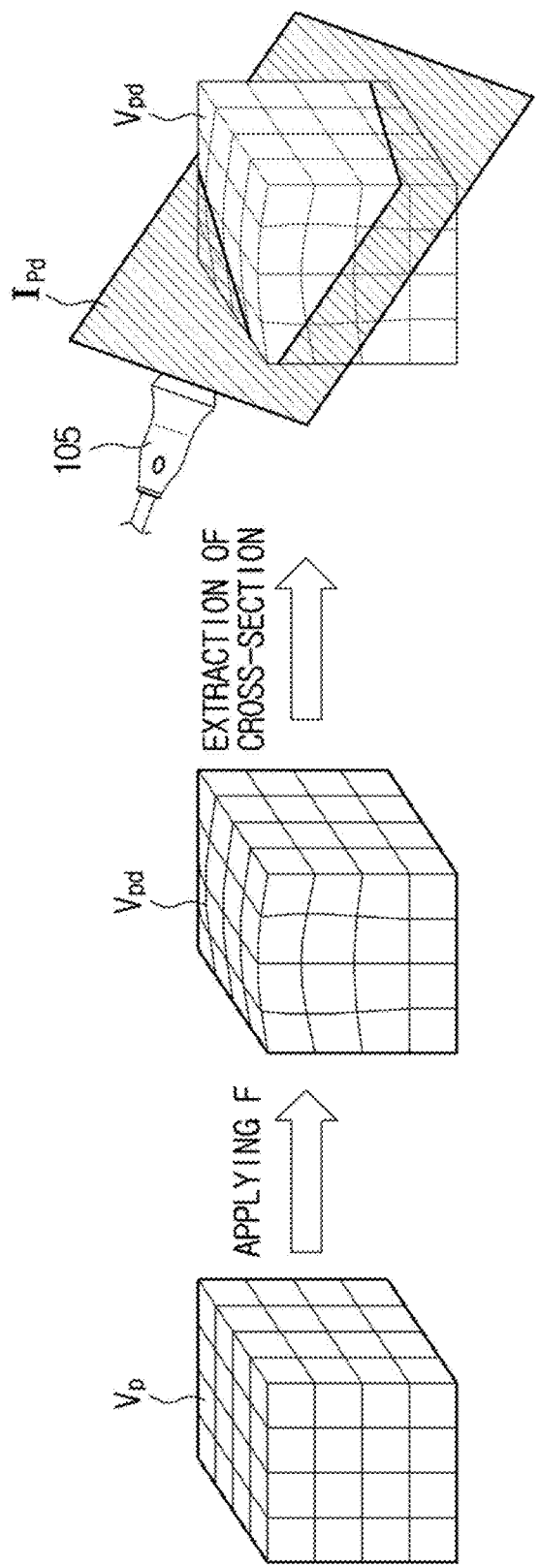

As illustrated in FIG. 15, the image transformator may apply the transformation of the patient adaptive object model to the second image data $V_P$ of the target patient. The second image data $V_P$ of the target patient may be transformed by directly applying the estimated force to the second image data of the target patient. FIG. 15 illustrates that the transformation of the patient adaptive object model is applied to entire 3D volume data of the patient.

The image registrator may perform image registration by acquiring a cross-sectional image $I_{pd}$ corresponding to an ultrasound image of the patient from the transformed second image data $V_{pd}$.

Figure 16:
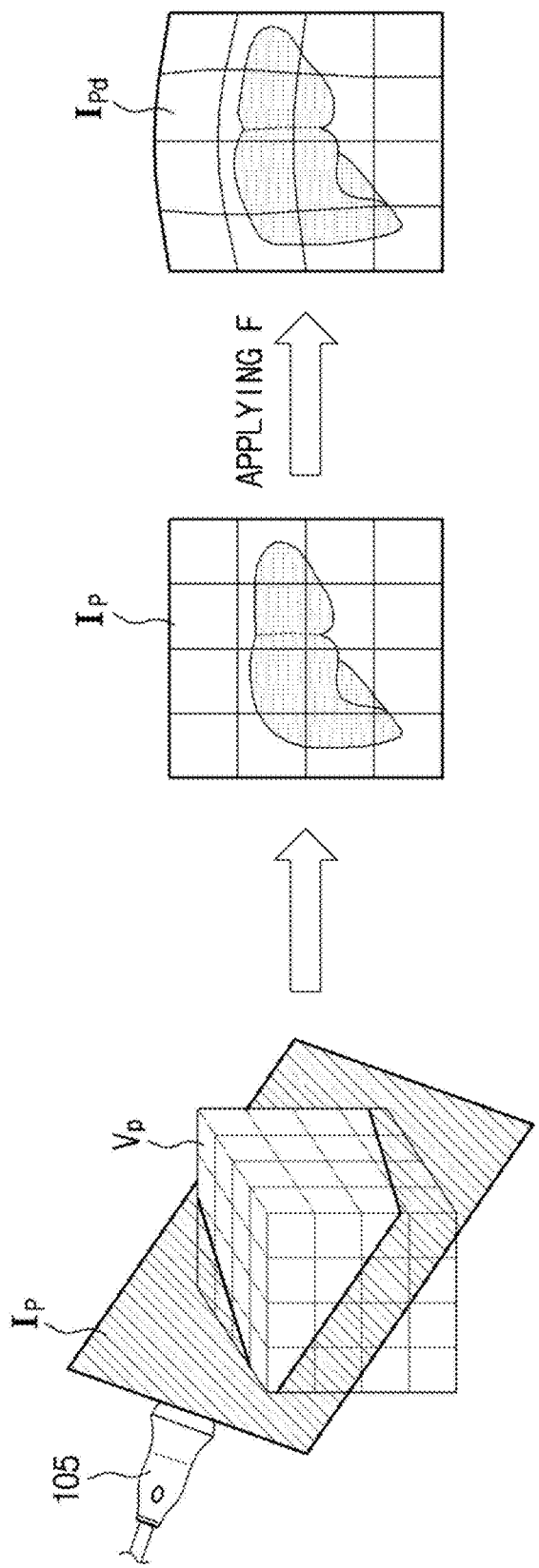

Alternatively, as illustrated in FIG. 16, after extracting the cross-sectional image corresponding to an ultrasound image of the patient from the transformed second image data, the transformation of the patient adaptive object model may be applied to the extracted cross-sectional image. Alternatively, the estimated force distribution may be directly apply to the extracted cross-sectional image of the target patient so that the extracted cross-sectional image of the target patient to be transformed.

As illustrated in FIGS. 15 and 16, image registration with high-definition may be performed since the second image may be transformed by applying the present respiratory phase of the target patient and the physical properties of the liver of the target patient.

As described above, the image fuser may directly generate a patient adaptive object model, but this is not limiting and a patient adaptive object model may be generated in a second medical imaging apparatus, a central server device, i.e., PASC, a user computer, and other external apparatus, to be transmitted to a medical imaging apparatus. The storage unit of the medical imaging apparatus may temporarily or non-temporarily store a patient adaptive object model transmitted from the external apparatus, and the image fuser may transform the second image of the target patient by using the stored patient adaptive object model and the first image. The operation of the transformation of the second image is the same as the operation of image transformator, and thus a further detailed description will be omitted.

Figure 17:
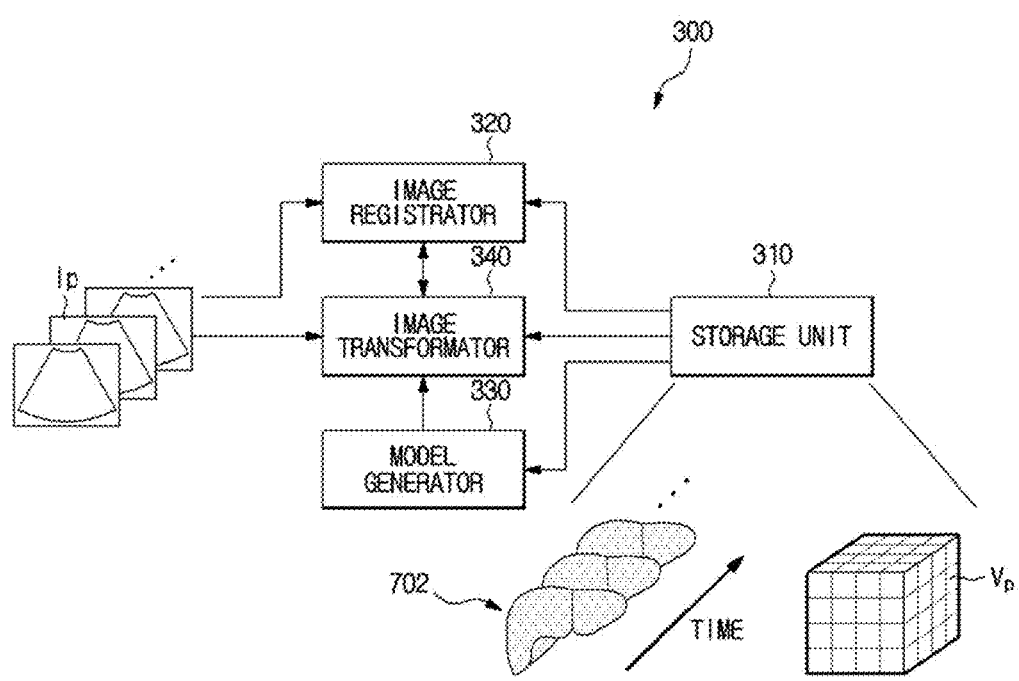
FIG. 17 is a control block diagram illustrating an image processing apparatus according to an exemplary embodiment.

FIG. 17 is a control block diagram illustrating an image processing apparatus according to an exemplary embodiment.

Referring to FIG. 17, an image processing apparatus 300 according to an exemplary embodiment may include a storage unit 310 to store second image data $V_P$ of the patient and a statistical object model 702, an image registrator 320 to perform image registration between a first image and a second image of the patient, a model generator 330 to generate a patient adaptive object model by applying the statistical object model to the second image data of the patient, and an image transformator 340 to transform the second image of the patient according to the present respiration phase of the patient.

The second image data $V_P$ of the patient may be acquired by the second imaging apparatus in advance before a first image of the patient is taken, and/or may be 3D volume data.

The statistical object model may be generated by building a standard model related to the shape of the organs and the changes of position by acquiring the statistical distribution of changes in positions corresponding to each location of organs from 4D medical images taken from a number of patients, as described above. The statistical object model may be generated in the model generator 330, but is not limited thereto.

The storage unit 310 may be similar to the storage unit 120.

The image registrator 320 may search the second image corresponding to the first image to display the first image along with the second image in which the first image and the second image correspond to each other, and may perform image registration to match the position of the first image and the second image. The image registration between the first image and the second image may be performed before or after applying transformation of an object caused by the certain movement of the patient to the second image.

The model generator 330 may generate a patient adaptive object model by applying the statistical object model stored in the storage unit 310 to the second image data of the patient. Particularly, the model generator 330 may acquire a parameter of the movement probability distribution, which is related to which position each point of the organ of the target patient is moved to in a certain respiratory phase, and may acquire a patient adaptive object model by applying the acquired parameter to the movement probability distribution of the statistical object model. Therefore, the patient adaptive object model may include statistical probability information related to how to the object of the patient is transformed according to the respiratory phase.

The image transformator 340 may transform the second image by correcting the difference between the first image of the target patient acquired in real time and the patient adaptive object model. Particularly, the image transformator 340 may extract the shape of the organ corresponding to the present respiratory phase of the target patient from the patient adaptive object model, and may detect a target object from an ultrasound image of the patient, which is to be compared with the extracted shape of the organ. When the organ is not clearly displayed on the first image, other organ, which is replaceable with the organ, may be detected. For example, when the object of interest is the liver, and the first image is an ultrasound image, the diaphragm may be detected instead of the liver when the boundary of the liver is not clearly displayed on the ultrasound image. The image transformator may calculate differences between the shape of the liver extracted from the patient adaptive object model and the diaphragm detected from the ultrasound image, and may estimate the force f to correct the calculated differences. The image transformator may transform the second image of the patient by using the estimated force.

Particularly, for transformation of the second image of the patient by using the estimated force, a physical model, to which the physical properties of the organ of the patient are applied, may be used. The transformation of the organ of the patient may be estimated by applying the estimated force to the physical model, and the estimated transformation of the organ may be applied to the second image data or the second image. Here, estimating the transformation of the organ may represent transforming the patient adaptive object model. Since the image transformator 340 may transform the image by applying the physical model to which the physical properties of the organ of the patient are applied, the image registration with high-definition may be performed although the condition of the organ of the patient is different from the statistical object model.

The image registrator 320, the model generator 330, and the image transformator 340 may be implemented by a processor configured to process data according to programs configured to perform each operation wherein the programs configured to perform each operation may be stored in a memory. The memory may be the same as the memory of the storage unit 310, or may be separately provided. The image registrator 320, the model generator 330, and the image transformator 340 may be implemented by a separate processor or may share one or more processors.

The components of the above-described image processing apparatus 300 may perform the same operations as the components of the medical imaging apparatus 100. Accordingly, described above with reference to the exemplary embodiments of the medical imaging apparatus 100 is applicable to the image processing apparatus 300.

A patient adaptive object model may be generated in other external apparatus other than the image processing apparatus and transmitted. In this case, the model generator may be excluded from the image processing apparatus, and the storage unit may temporarily or non-temporarily store the patient adaptive object model transmitted from the other external apparatus.

The image processing apparatus 300 may be included into the medical imaging apparatus, such as an ultrasound imaging apparatus, an OCT apparatus, an MRI apparatus, an X-ray imaging apparatus, a SPECT apparatus, and a PET apparatus, but is not limited thereto. The image processing apparatus 300 may be included into a user computer and/or a central server.

Figure 18:
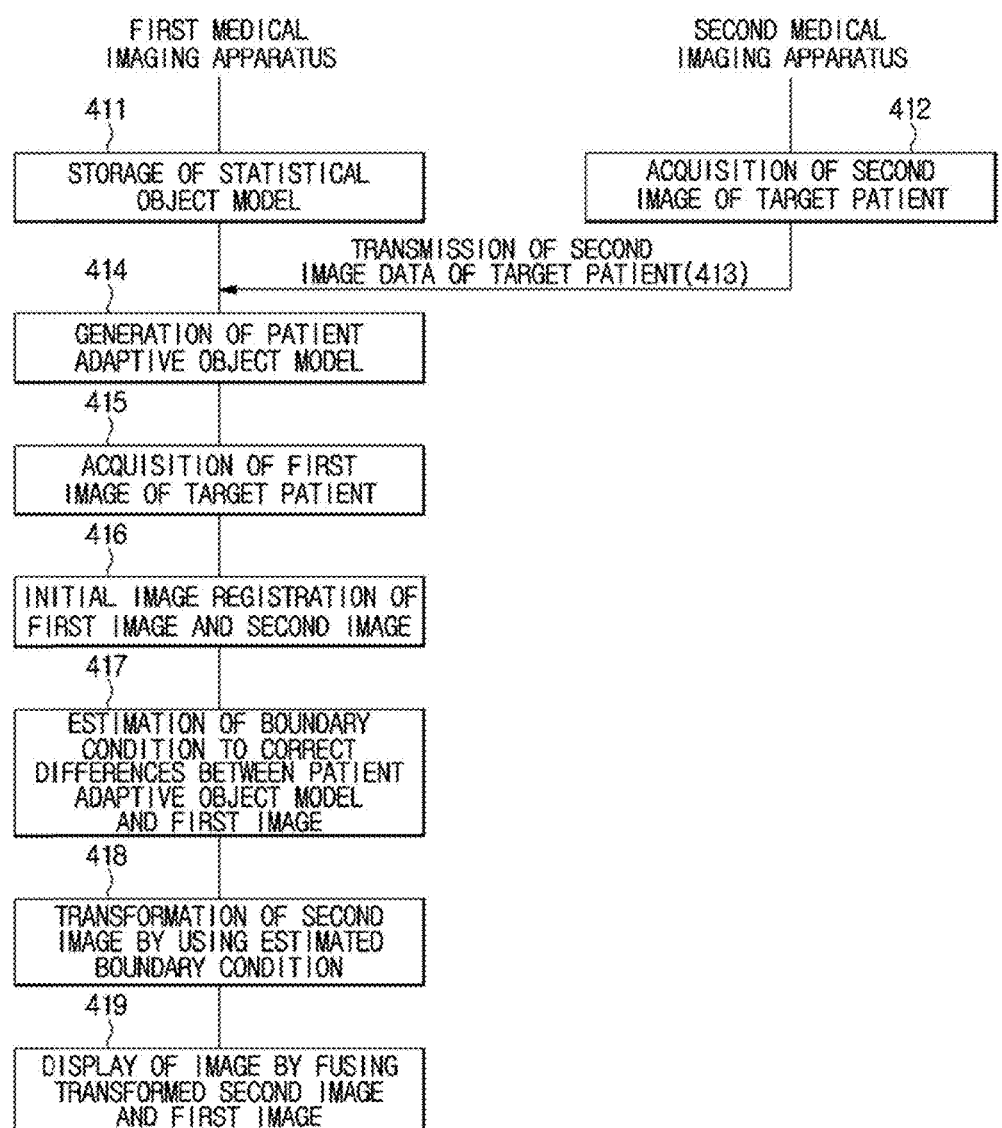
FIG. 18 is a flowchart illustrating an example of an image fusion method according to an exemplary embodiment.

FIG. 18 is a flowchart illustrating an example of an image fusion method according to an exemplary embodiment.

Referring to FIG. 18, the first medical imaging apparatus stores a statistical object model (operation 411) which may be generated by building a standard model related to the shape of the organ and the changes of position by acquiring the statistical distribution of changes in positions corresponding to each location of the organ from 4D medical images taken from a number of patients as described above. The statistical object model may be generated in the first medical imaging apparatus or may be generated in other external apparatus and to be transmitted.

The second medical imaging apparatus may acquire second image data of the patient (operation 412), and the second image data of the patient may be transmitted to the first medical imaging apparatus (operation 413). The second medical data may be 3D volume data. The second image data of the patient may be transmitted from the second medical imaging apparatus to the first medical imaging apparatus via local area communication, wired communication, and wireless communication, or via a storage medium, such as a USB. The second image data may be directly transmitted from the second medical imaging apparatus to the first medical imaging apparatus or may be transmitted via a medium, such as a PACS.

The first medical imaging apparatus generates a patient adaptive object model by using the statistical object model and the second image data of the patient (operation 414). Since the statistical object model may be acquired from other patients and not the patients themselves, the first medical imaging apparatus may generate a patient adaptive object model including information related to how to the object of the patient is transformed according to the respiratory phase by applying second image data of the patients themselves to the statistical object image. Particularly, the first medical imaging apparatus may acquire a parameter of the movement probability distribution, which is related to which position each point of the organ of the patient is moved to in a certain respiratory phase, and may generate a patient adaptive object model by applying the acquired parameter to the movement probability distribution of the statistical object model.

The first medical imaging apparatus acquires a first image of the patient (operation 415). The first image may be acquired in real time, and the transformation caused by a periodic movement, such as a respiration, and a heartbeat, may be displayed on the first image.

The first medical imaging apparatus may perform initial image registration between the first image and the second image (operation 416). But, this is not limiting and the image registration between two images may be performed after performing the transformation of the second image. The method of the image registration is not limited thereto, and thus any method known to those skilled in the art may be applied.

The first medical imaging estimates a boundary condition to correct differences between the patient adaptive object model and the first image (operation 417), and transforms the second image by using the estimated boundary condition (operation 418). The estimated boundary condition may be a force and when the second image is transformed by using the estimated boundary condition, a physical model to which the properties of the organ of the patient are applied may be used.

The first medical imaging apparatus displays the image by fusing the transformed second image and the first image (operation 419). Two images may be fused in a variety of methods. For example, two images may be displayed to be overlapped, or to be arranged side by side vertically or horizontally. The method of the image fusion is not limiting, and thus any appropriate method known to those skilled in the art in the art may be applied.

Some of the operations illustrated in the flowchart of FIG. 18 may be omitted, and the image fusion method according to an exemplary embodiment may selectively include some operations illustrated in the flowchart of FIG. 18. For example, only operations 411, 414, 415, 416, 417, 418, and 419 performed in the first medical imaging apparatus may be included in the image fusion method according to an exemplary embodiment.

Figure 19:
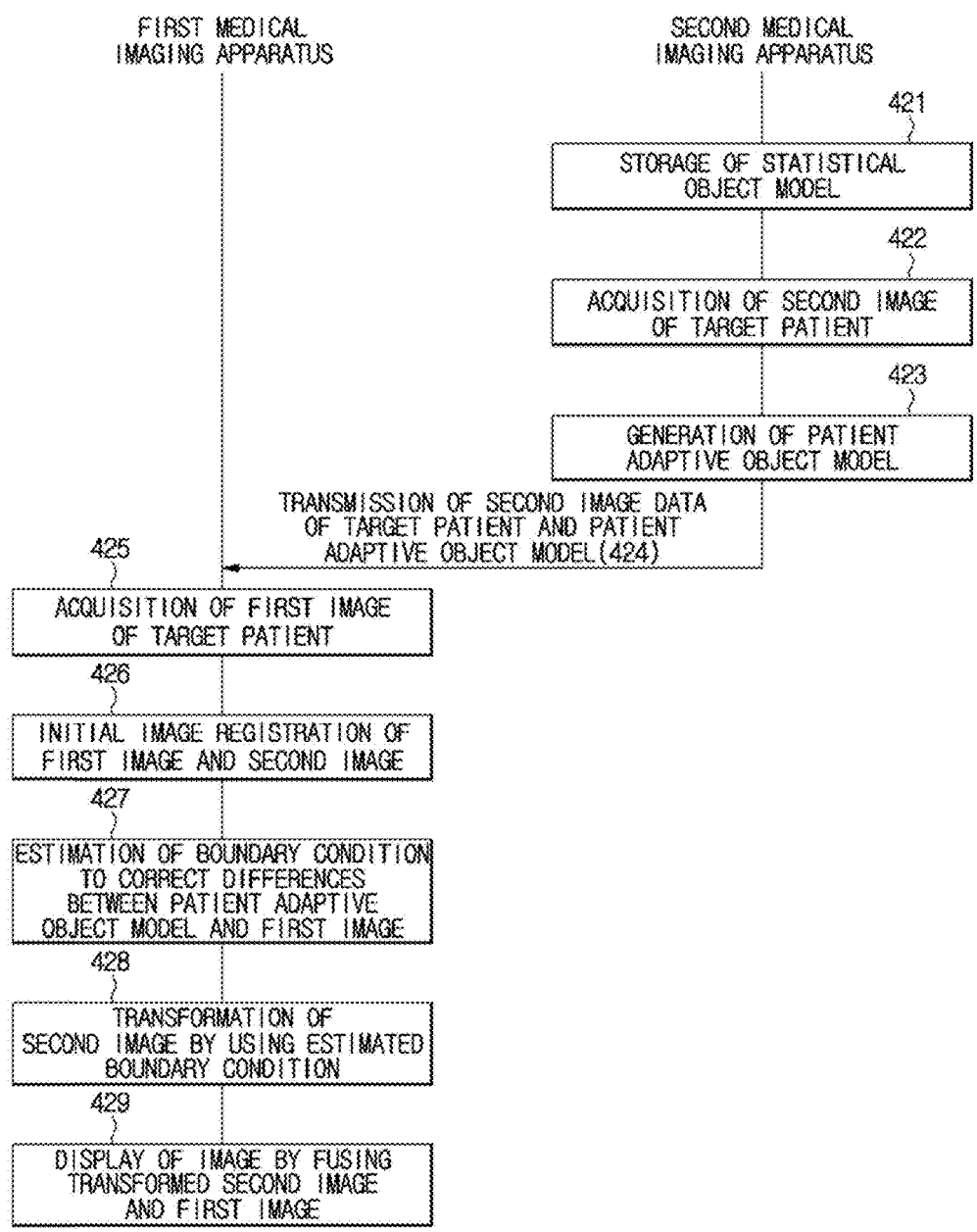
FIG. 19 is a flowchart illustrating another example of an image fusion method according to an exemplary embodiment.

FIG. 19 is a flowchart illustrating another example of an image fusion method according to an exemplary embodiment.

Referring to FIG. 19, a statistical object model may be stored in a second medical imaging apparatus (operation 421). When a second image data of the patient is acquired (operation 422), the second medical imaging apparatus generates a patient adaptive object model by applying the statistical object model to the second image data of a patient (operation 423). The second image data of the patient and the patient adaptive object model may be transmitted to the first medical imaging apparatus (operation 424).

The first medical imaging apparatus may acquire a first image of the patient (operation 425), and may perform initial image registration between the first image and the second image (operation 426). The first medical imaging apparatus estimates a boundary condition to correct differences between the patient adaptive object model and the first image (operation 427), and transforms the second image by using the estimated boundary condition (operation 428). The first medical imaging apparatus fuses the transformed second image and the first image and displays the fused image (operation 429).

Some of the operations illustrated in the flowchart of FIG. 19 maybe omitted, and the image fusion method according to an exemplary embodiment may selectively include some of the operations illustrated in the flowchart of FIG. 19. For example, only operations 425, 426, 427, 428, and 429 performed in the first medical imaging apparatus may be included in the image fusion method according to an exemplary embodiment.

Figure 20:
FIG. 20 is a flowchart illustrating another example of an image fusion method according to an exemplary embodiment.

FIG. 20 is a flowchart illustrating another example of an image fusion method according to an exemplary embodiment.

Referring to FIG. 20, a statistical object model may be stored in other apparatus, i.e., a computer 20, for example, a user's computer or PACS, and not in the first medical imaging apparatus or the second medical imaging apparatus (operation 431). The statistical object model may be generated in other apparatus or may be transmitted from another apparatus. The statistical object model may be generated by building a standard model related to the shape of the organ and the changes of position by acquiring the statistical distribution of changes in positions corresponding to each location of the organ from 4D medical images taken from a number of patients. Particularly, an image acquired in each respiratory phase is extracted from 4D medical images taken from a number of patients, the image is restructured to be carried on resampling and thereby the correspondence between the organs of the patient may be acquired.

The second medical imaging apparatus acquires second image data of the patient (operation 432), and transmits the second image data of the patient to other apparatus (operation 433). When the second image data is transmitted from the second medical imaging apparatus to other apparatus, a wireless communication, a wired communication, or a local area communication, may be used or a storage medium, i.e., a USB may be used.

Other apparatus receiving the second image data of the patient generates a patient adaptive object model by applying the statistical object model to the second image data of the patient (operation 434). Other apparatus transmits the patient adaptive object model and the second image data of the patient to the first medical imaging apparatus (operation 435). Alternatively, the second image data may be transmitted from the second medical imaging apparatus to the first medical imaging apparatus, and other apparatus may transmit only the patient adaptive object model to the first medical imaging apparatus.

The first medical imaging apparatus may acquire a first image of the patient (operation 436), and may perform initial image registration between the first image and the second image (operation 437). The first medical imaging apparatus may estimate a boundary condition to correct differences between the patient adaptive object model and the first image (operation 438), and transforms the second image by using the estimated boundary condition (operation 439). The first medical imaging apparatus fuses the transformed second image and the first image and displays the fused image (operation 440).

Some of operations illustrated in the flowchart of FIG. 20 may be omitted and the image fusion method according to an exemplary embodiment may selectively include some of the operations illustrated in the flowchart of FIG. 20. For example, only the operations 436, 437, 438, 439 and 440 performed in the first medical imaging apparatus may be included in the image fusion method according to an exemplary embodiment.

Figure 21:
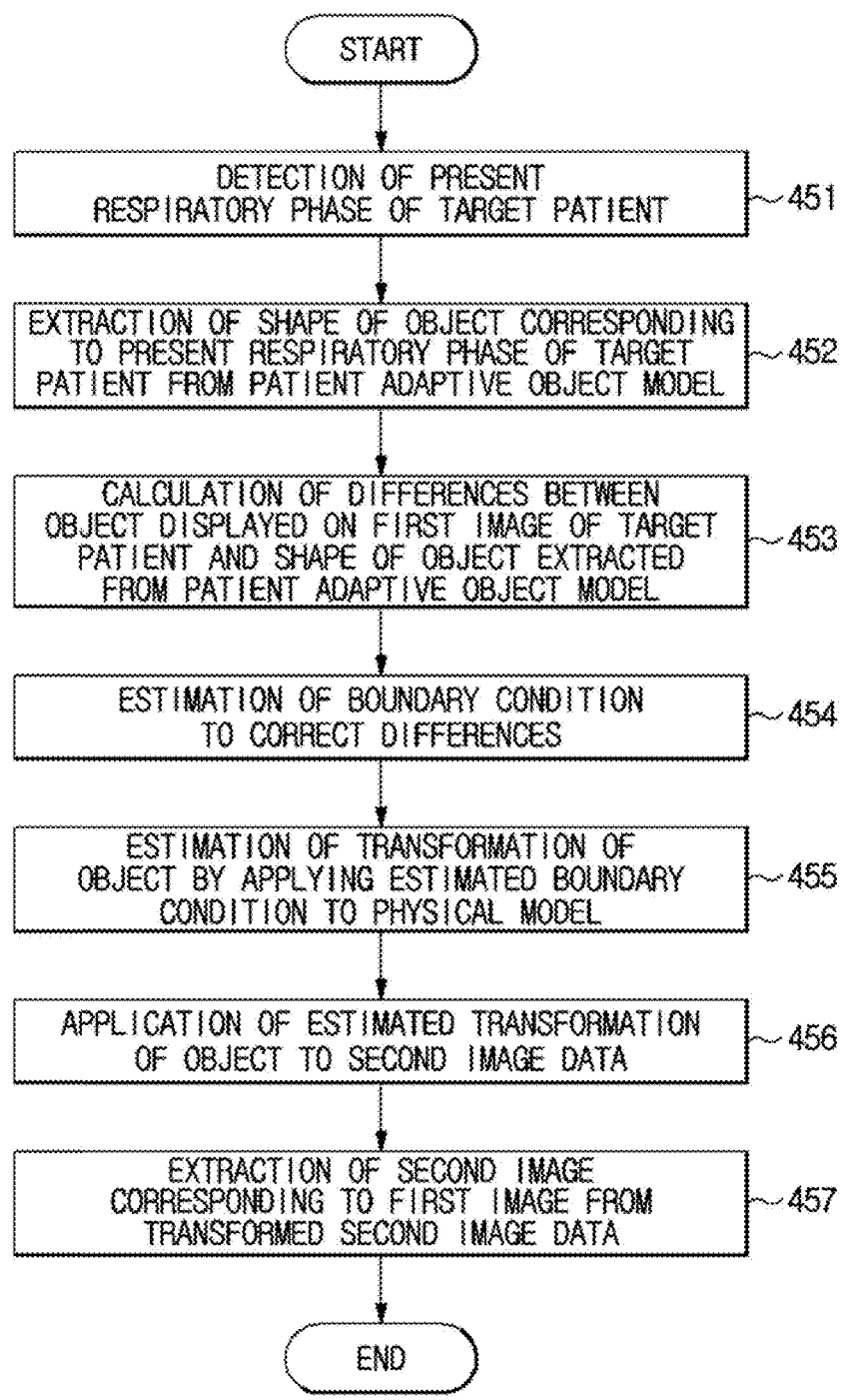
FIGS. 21 and 22 are flowcharts illustrating a process of transforming a second image in an image fusion method according to an exemplary embodiment.
Figure 22:
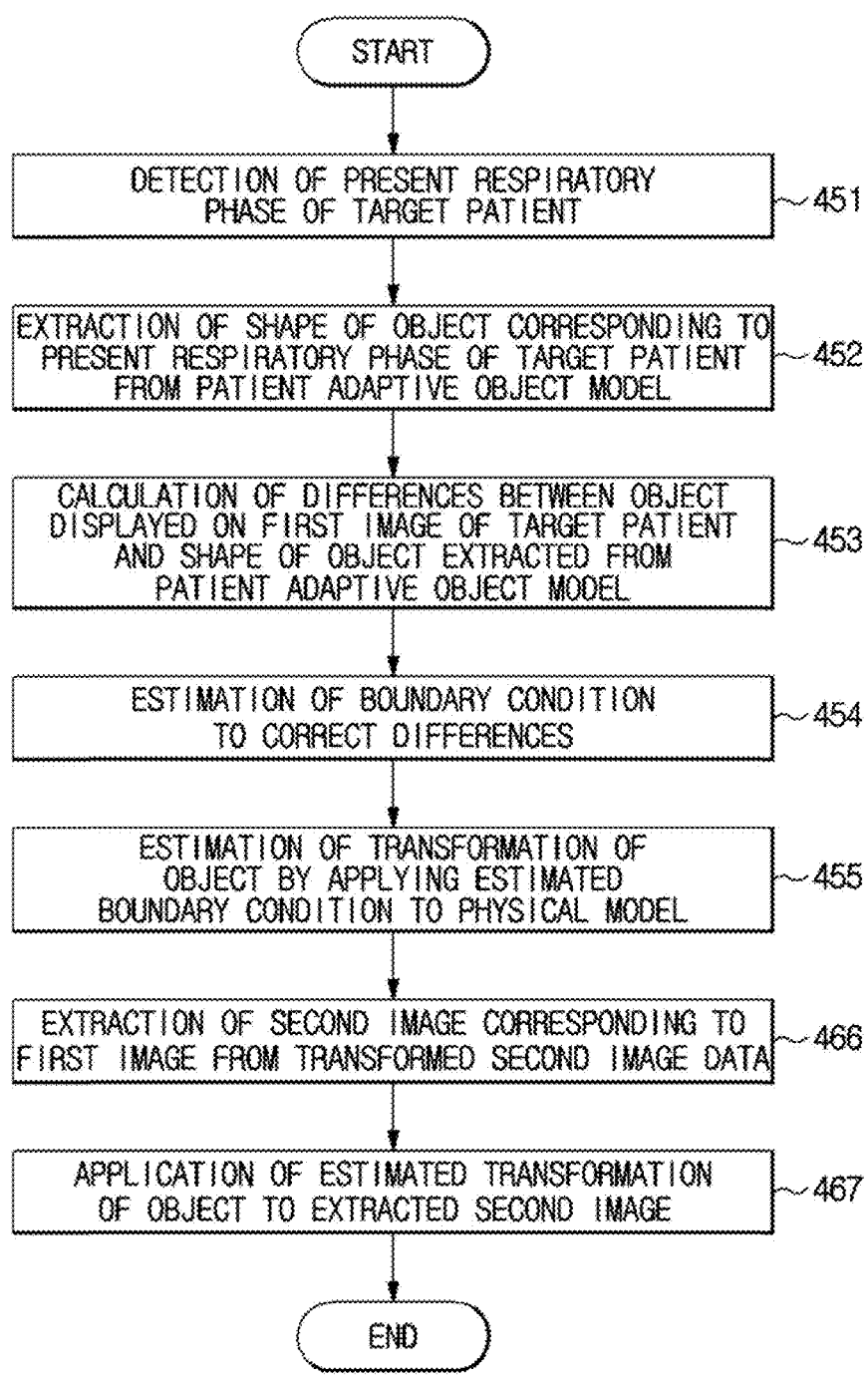

FIGS. 21 and 22 are flowcharts illustrating a process of transforming a second image in an image fusion method according to an exemplary embodiment. A flowchart of FIG. 21 illustrates estimating a boundary condition to correct differences between the patient adaptive object model and the first image, and transforming the second image by applying the estimated boundary condition in the above-mentioned image fusion method according to FIGS. 18 to 20.

Referring to FIG. 21, a present respiratory phase of a target patient is detected (operation 451). The respiration of the patient may be measured by respiration measurement apparatus, such as optical tracker, respiratory belt, and spirometer. However, the image fusion method is not limited thereto, and any appropriate methods known to those skilled in the art may be used for measuring the respiration of the patient.

The shape of an object corresponding to the present respiratory phase of the target patient is extracted from the patient adaptive object model (operation 452).

The differences between an object displayed on the first image and the shape of the object extracted from the patient adaptive object model is calculated (operation 453). For example, a target object is extracted from the first image of a patient, which is to be compared with the shape of the object extracted from the patient adaptive object model. When the object is clearly displayed on the first image, the extracted shape of the object may be directly compared with the object displayed on the first image. However, when a boundary of the object is not clear in the first image, the first medical imaging apparatus may detect other object, which is clearly displayed on the first image to be used in place of the shape of the object. For example, when the object is the liver, the diaphragm placed just over the liver may be detected as a target object.

A boundary condition to correct differences is estimated (operation 454). For example, the boundary condition may be a force.

The transformation of the object is estimated by applying the estimated boundary condition to a physical model (operation 455). The physical model is formed by applying the properties of the object of the patient, may be generated based on the shape of the object extracted from the second image data, and the degree of elasticity of the object, and may be represented by Equation 1. The transformation of the object may be estimated by applying the estimated boundary condition to the physical model to which the properties of the object of the patient are applied.

The second image data is transformed by applying the estimated transformation of the object to the second image data (operation 456), and a second image corresponding to the first image is extracted from the transformed second image data (operation 457).

Alternatively, it may be possible to transform the second image data after extracting a second image from the second image data, and an example thereof is illustrated in FIG. 22.

Referring to FIG. 22, operations 451 to 455 are the same as an example illustrated in FIG. 21, and thus a detailed description thereof will be omitted.

After a second image corresponding to the first image of a patient is extracted from the second image data (operation 466), the extracted second image may be transformed by applying the estimated transformation of the object (operation 467).

According to the medical imaging apparatus, an image processing apparatus, and an image fusion method of exemplary embodiments, when performing image registration between two images, which have a different modality from each other, a pre-acquired structure image is transformed by applying the transformation of the organ displayed on an image acquired in real time so that the accuracy of image registration may be improved.

In addition, when transforming an image, a statistical object model built from data of a number of patients, and a physical model, to which the properties of the organ of the patient are applied, are combined and applied so that image registration with high-definition may be performed.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical imaging apparatus comprising:
   a memory configured to store a patient adaptive object model in which a statistical object model related to transformation of an object caused by a periodic movement is applied to characteristics of the object of a target patient; and
   a processor configured to acquire a first image of the target patient, control a display to display the first image, calculate differences between a boundary of a shape of the object extracted from the patient adaptive object model and a boundary of a shape of the object displayed on the first image, and transform a second image of the target patient based on the calculated differences,
   wherein the processor is configured to transform the patient adaptive object model by applying a boundary condition, to correct the differences, to a physical model to which properties of the object of the target patient are applied.

2. The medical imaging apparatus of claim 1, wherein the processor is configured to generate the physical model based on the second image and a degree of elasticity of the object of the target patient.

3. The medical imaging apparatus of claim 1, wherein the processor is configured to generate transformation parameters of the patient adaptive object model, and transform the second image by applying the transformation parameters.

4. The medical imaging apparatus of claim 1, wherein the processor is configured to perform image registration between the transformed second image and the first image, to match the second image and the first image with one another, and control the display to display the matched first and second images.

5. The medical imaging apparatus of claim 1, wherein the periodic movement is a respiration divided into phases which are consecutive in time and include a present respiratory phase, and the processor is configured to extract the shape of the object corresponding to the present respiratory phase of the target patient from the patient adaptive object model, and transform the second image based on the differences in the extracted shape and the shape of the object in the first image.

6. The medical imaging apparatus of claim 1, wherein the processor is configured to acquire a parameter of a movement probability distribution, which includes information about a position to which each point of the object of the target patient is moved in a certain movement phase, and generate the patient adaptive object model by applying the acquired parameter to the movement probability distribution of the statistical object model.

7. The medical imaging apparatus of claim 3, wherein the memory is configured to store three-dimensional (3D) volume data including the second image.

8. The medical imaging apparatus of claim 7, wherein the processor is configured to transform the 3D volume data by applying the transformation parameters, and extract the second image corresponding to the first image of the target patient from the transformed 3D volume data.

9. The medical imaging apparatus of claim 7, wherein the processor is configured to extract the second image corresponding to the first image of the target patient from the 3D volume data, and transform the extracted second image by applying the transformation parameters.

10. The medical imaging apparatus of claim 1, wherein the processor is configured to acquire the first image of the target patient in real time.

11. The medical imaging apparatus of claim 1, wherein the first image is an ultrasound image, and the second image is one among a magnetic resonance imaging (MRI) image, a computed tomography (CT) image, and an optical coherence tomography (OCT) image.

12. An image processing apparatus configured to fuse images having modalities different from each other, the image processing apparatus comprising:

a memory configured to store a patient adaptive object model which is a transformed statistical object model related to transformation of an object caused by a periodic movement adapted to characteristics of the object of a target patient; and a processor configured to control a display to display a first image of the target patient, calculate differences between a boundary of a shape of the object extracted from the patient adaptive object model and a boundary of a shape of the object displayed on the first image, transform a second image of the target patient based on the calculated differences, wherein the processor is configured to transform the patient adaptive object model by applying a boundary condition, to correct the differences, to a physical model to which properties of the object of the target patient are applied.

13. The image processing apparatus of claim 12, wherein the processor is configured to generate the physical model based on the second image and a degree of elasticity of the object of the target patient.

14. The image processing apparatus of claim 12, wherein the processor is configured to generate transformation parameters of the patient adaptive object model, transform the second image by applying the transformation parameters of the patient adaptive object model, and perform image registration between the transformed second image and the first image.

15. The image processing apparatus of claim 12, wherein the periodic movement is a respiration divided into phases which are consecutive in time and include a present respiratory phase, and the processor is configured to extract the shape of the object corresponding to the present respiratory phase of the target patient from the patient adaptive object model, and transform the second image based on the differences between the extracted shape and the shape of the object displayed on the first image.

16. An image fusion method to fuse a first image and a second image, which has a modality different from the first image, the image fusion method comprising:

storing a patient adaptive object model which is a transformed statistical object model related to transformation of an object caused by a periodic movement adapted to characteristics of the object of a target patient;

displaying the first image of the target patient;

calculating differences between a boundary of a shape of the object extracted from the patient adaptive object model and a boundary of a shape of the object displayed on the first image; and transforming the second image of the target patient based on the calculated differences, wherein the transforming the second image comprises:

transforming the patient adaptive object model by applying a boundary condition, to correct the differences, to a physical model to which properties of the object of the target patient are applied.

17. The image fusion method of claim 16, wherein the transforming the second image comprises:

generating the physical model based on the second image and a degree of elasticity of the object of the target patient.

18. The image fusion method of claim 16, wherein the transforming the second image comprises:

generating transformation parameters of the patient adaptive object model; and transforming the second image by applying the transformation parameters.

19. The image fusion method of claim 16, further comprising:

performing image registration between the transformed second image and the first image; and displaying the registered first and second images on a display.

20. The image fusion method of claim 16, wherein the periodic movement is a respiration divided into phases which are consecutive in time and include a present respiratory phase, and the transforming the second image further comprises:

extracting the shape of the object corresponding to the present respiratory phase of the target patient from the patient adaptive object model, and transforming the second image based on the differences between the extracted shape and the shape of the object displayed on the first image.

21. An apparatus comprising:

a medical imaging apparatus configured to generate a first image of a target patient by emitting ultrasound signals to the target patient and receiving reflected ultrasound signals from the target patient;

a memory configured to store a second image of the target patient captured by using imaging conditions different from that of the first image;

a display configured to display at least one among the first image and the second image; and a processor which is programmed to:

generate a patient adaptive object model for the target patient by applying a physical characteristic of an object of the target patient to a statistically obtained object model, which represents an object distortion caused by a periodic biological movement;

transform the second image based on a first object extracted from the patient adaptive object model, to which the physical characteristic of the object of the target patient has been applied, and a second object, which corresponds to the first object and is displayed on the first image;

register the first image with the transformed second image; and control the display to display the first image and the second image registered with one another, wherein the periodic biological movement is a respiration, the statistically obtained object model is a model which is obtained based on images of different patients processed for each of consecutive breathing phases of the respiration, and stored in the memory prior to obtaining the first image, and the patient adaptive object model is generated by adjusting the statistically obtained object model based on the second image of the target patient.

22. The apparatus of claim 21, wherein the first object and the second object are different biological objects.

23. The apparatus of claim 21, wherein the first object and the second object are the same biological objects.

24. The medical imaging apparatus of claim 1, wherein the processor is configured to generate the patient adaptive object model for the target patient by applying a physical property of the object of the target patient to the statistical object model, which is statistically obtained based on images of different patients.

* * * * *